US005654799A

United States Patent [19]
Chase et al.

[11] Patent Number: 5,654,799
[45] Date of Patent: Aug. 5, 1997

[54] METHOD AND APPARATUS FOR MEASURING AND CONTROLLING THE SURFACE CHARACTERISTICS OF SHEET MATERIALS SUCH AS PAPER

[75] Inventors: Lee M. Chase, Los Gatos; John D. Goss, San Jose, both of Calif.

[73] Assignee: Measurex Corporation, Cupertino, Calif.

[21] Appl. No.: 435,995

[22] Filed: May 5, 1995

[51] Int. Cl.$^6$ ............................................. G01N 21/86
[52] U.S. Cl. ................................... 356/371; 356/429
[58] Field of Search ..................... 356/429, 430, 356/431, 371, 446; 250/559.01, 559.22, 559.23, 559.27, 559.39

[56] References Cited

U.S. PATENT DOCUMENTS

| | | | |
|---|---|---|---|
| 3,469,104 | 9/1969 | Hector | 356/430 |
| 3,606,541 | 9/1971 | Sugano et al. | |
| 3,999,860 | 12/1976 | Demsky et al. | 356/446 |

(List continued on next page.)

FOREIGN PATENT DOCUMENTS

| | | |
|---|---|---|
| 677739A | 10/1995 | European Pat. Off. |
| 3412108 | 10/1984 | Germany |
| WO9306300 | 4/1993 | WIPO |

OTHER PUBLICATIONS

Erik Lindem, "How Biaxial Drying Strategy Influences the Surface Properties of Laboratory Sheets", The Norwgian Pulp and Paper Research Institute.

John E. Maley, "The Effect of Paper Properties on Print Quality", John E. Maley, Coating Binders 1990, pp. 3–6.

Dr. Terry Purdy, "Taking the Rough with the Smooth", Paper, May 1993, pp. 33–36.

R.H. Crotogino, "Supercalendered and Conventionally Calendered Newsprint—A Comparison of Surface and Printing Properties", The Pulp and Paper Research Institute of Canada, pp. 89–94.

Hideki Fujiwara and Chizuru Kaga, "Single and Double Blade Coating: The Variations in Sub–millimeter Scale and Their Effects on Sheet and Print Qualities", Jujo Paper Co., Ltd., 1992 Coating Conference, pp. 147–159.

(List continued on next page.)

*Primary Examiner*—Richard A. Rosenberger
*Attorney, Agent, or Firm*—Loeb & Loeb LLP

[57] ABSTRACT

An on-line laser triangulation position sensing system provides measurements of the surface features of a moving sheet such as paper. The measurements are correlatable with measurements made with standard laboratory surface smoothness testers and provide predictions of the printability of paper during its fabrication. The sensing system includes a segmented balance detector having a high frequency response. The sensing system further includes signal processing circuitry comprising a plurality of channels, each channel including a filter. The various filters have different cutoff frequencies for passing different frequency spectra representing ranges of surface feature scale sizes. The cutoff frequency of each filter is varied in response to variations in sheet speed. The sheet sensing system further includes a sheet stabilizer to minimize flutter in the measurement region and a standardizing member permitting performance verification of the sensor system at at least one scale size spectrum. The sensing system may also be provided with a sheet compressor to compress the sheet in the measurement region so as to simulate the pressures applied to sheet samples by laboratory air leak smoothness testers. The output of the position sensing system may be used in conjunction with various kinds of papermaking machines to control one or more of the many papermaking process parameters that determine the smoothness or texture of the final product. The sensing system can be used to measure tissue crepe and such measurement can be utilized to control various crepe-determining stages in a tissue making machine and to monitor the condition of the creping or doctor blade in such a machine.

45 Claims, 15 Drawing Sheets

U.S. PATENT DOCUMENTS

| | | | |
|---|---|---|---|
| 4,015,904 | 4/1977 | De Remigis | 356/243 |
| 4,019,066 | 4/1977 | Lucas et al. . | |
| 4,029,419 | 6/1977 | Schumann et al. | 356/446 |
| 4,092,068 | 5/1978 | Lucas et al. . | |
| 4,102,578 | 7/1978 | Suzuki et al. . | |
| 4,276,766 | 7/1981 | Lucas et al. . | |
| 4,384,514 | 5/1983 | Larivé et al. . | |
| 4,434,649 | 3/1984 | Williams . | |
| 4,644,174 | 2/1987 | Ouellette et al. | 356/430 |
| 4,726,685 | 2/1988 | Kobayashi et al. | 356/445 |
| 4,760,271 | 7/1988 | Brenholdt | 250/571 |
| 4,770,536 | 9/1988 | Golberstein | 356/371 |
| 4,798,469 | 1/1989 | Burke . | |
| 4,875,769 | 10/1989 | Linebarger | 356/28 |
| 4,965,452 | 10/1990 | Sturm . | |
| 4,978,861 | 12/1990 | Sabator et al. | 356/371 |
| 5,024,529 | 6/1991 | Svetkoff et al. | 356/376 |
| 5,029,469 | 7/1991 | Chase et al. | 73/159 |
| 5,092,678 | 3/1992 | Chase et al. . | |
| 5,110,212 | 5/1992 | Gabura . | |
| 5,118,955 | 6/1992 | Cheng | 250/559.23 |
| 5,182,743 | 1/1993 | Tinet . | |
| 5,243,407 | 9/1993 | King et al. . | |
| 5,243,849 | 9/1993 | Williams . | |
| 5,355,083 | 10/1994 | George et al. . | |

OTHER PUBLICATIONS

"Point Range Sensors", CyberOptics Corporation advertising materials, 1986.

"Position Sensors", Technical Data Sheet, Silicon Detector Corporation.

Dipl. Ing. Sylvia Schmidt, "Smoothness Measurement in Paper Making and Printing", Paper, Apr. 19, 1982.

Sheffield, "Smoothness of Paper", Tappi, Jul. 1970, vol. 53, No. 7.

Donald L. Stradley, "Predicting Printability", Emveco, Inc., Tappi Symposium, 1989 Process and Product Quality Division, pp. 75–78.

Gane, P.A.C., "Mottle and the influence of coating and binder migration", Paper Technology, Apr., 1989.

FIG. I

METHOD AND APPARATUS FOR MEASURING AND CONTROLLING THE SURFACE CHARACTERISTICS OF SHEET MATERIALS SUCH AS PAPER

1. FIELD OF THE INVENTION

The present invention relates to methods and apparatus for measuring and controlling, on-line and in non-contact fashion, certain characteristics, such as smoothness, of the surface of a traveling sheet such as a paper web.

2. BACKGROUND OF THE INVENTION

The surface characteristics of paper are important to both manufacturers and users of a broad range of paper products including printing grade paper, tissue, newsprint, linerboard, and so forth. For example, in the manufacture of paper and paperboard, printability is an important surface property to measure and control. Printability is not only important for printing grades of paper such as magazine paper and newsprint but also for linerboard and Kraft paper since, increasingly, the outside of boxes and bags are printed with manufacturers' logos and other information.

"Printability" refers to the characteristics of paper that make high quality printing possible. The properties affecting printability include, among others, surface smoothness and surface compressibility. Surface smoothness is considered the most important characteristic for all printing processes. High points on the surface tend not to hold ink because the pressure between the high points and the printing plate squeegees out the ink. Low points on the surface are unable to receive ink because they never contact the printing plate. With respect to surface compressibility, some printing processes such as rotogravure require a paper with a high degree of compressibility. The high pressure used in the printing press allows the surface to conform to the printing plate. Paper with a relatively rough surface in the uncompressed state can nevertheless have good printability qualities because of its surface compressibility.

Up to a point, increased smoothness, that is, decreased deviations from an ideal plane, enhances the printability of paper. A smooth surface tends to prevent ink from infiltrating the interstices of the paper fiber substrate in a fashion similar to the absorption of ink by an ink blotter. Thus, there is a significant relationship between the surface smoothness and print quality, that is, print density uniformity.

In the sense used herein, "smoothness" (and its complement, "roughness") refers to the microtopography of the surface of the sheet. Smoothness measurements are not concerned with the absolute location of the surface but rather with the extent to which the surface location deviates or varies from an ideal or mean plane. Such smoothness height variations are extremely small, being of the order of 10 micrometers. To obtain meaningful smoothness measurements, it is also necessary to know the scale size or interval (i.e., wavelength) over which the height variations occur. Small height variations occurring over a distance of several centimeters would have little effect on smoothness and consequently, printability, while the same variations occurring over only a 1 mm interval could have significant effects. For purposes of determining smoothness in the sense in which that term is used herein, it is most useful to determine height variations within several specific scale size ranges, for instance 20 to 100 micrometers, 100 to 200 micrometers, 200 to 400 micrometers, etc. Depending on the process, some scale size ranges will be more important than others.

Laboratory instruments have been developed which have achieved de facto standard status within the paper industry for the determination of surface smoothness. Because of their widespread popularity, it is desirable that any technique for determining paper smoothness on-line provides results that correlate well with the results produced by these recognized de facto standard laboratory instruments.

Traditionally, surface smoothness, as a predictor of printability, has been measured in the laboratory by various kinds of air leak tests, such as Sheffield, Parker Print Surf (PPS), BEKK and Bendtsen. The instruments used in these tests generally consist of a gas-confining wall or cylinder having an end surface placed in contact with the surface of a test sheet. Gas from a pressurized source is admitted into the cylinder and the rate at which the gas leaks past the interface of the cylinder end and paper surface is used as a determination of paper surface smoothness; obviously, the rougher the paper surface the faster the air escapes from the cylinder. The contacting surface of the air leak gauge may be a flat annular area or a knife edge and the leak rates will differ for these different contact surface geometries. Despite their popularity, air leak gauges tend not to work well with paper surfaces that are very smooth.

Recently, a new smoothness criterion called "Micro Average" was introduced by Emveco, Inc., Newberg, Oreg., U.S.A., and has found some industry acceptance for predicting printability of various paper products, particularly linerboard. Emveco manufactures a line of gauges for making surface profile measurements from which the "Micro Average" can be calculated. One such gauge uses a stylus having a radius of 0.00125 inch to measure the height of the sheet surface at a succession of points spaced along the test surface at equal intervals of, for example, 0.005 inch. As many as 500 readings or more are taken. The "Micro Average" is the average difference between successive readings over the entire set of readings.

Like the air leak testers, the Emveco gauge is a laboratory instrument that cannot be used on-line. Paper manufacturers, however, need a continuous indication of surface smoothness of the moving paper sheet as it is being produced. In this way, an immediate indication of printability is available, allowing the manufacturer to make corrections in the production process as needed in the event smoothness departs from a target value. Moreover, any such on-line measurements should correlate well with the results of standard laboratory tests.

Attempts have been made to satisfy the need for sensing smoothness on-line. In this connection, the prior art includes on-line, non-contact, optical surface roughness measuring apparatus. Most common are laser triangulation sensors in which a laser beam is focused on the surface to be measured. A lens focuses the image of the incident laser spot onto a position sensitive detector. The location of the image determines the location of the surface. The advantages of these prior art laser triangulation position sensors are their simplicity and accuracy. Among their disadvantages are, first, that the kind of position sensitive detectors typically used, CCDs and lateral cells, have limited frequency response and second, that as the surface position moves up and down (due to sheet "flutter", for example), the size of the spot changes since it goes out of focus; as a result, the scale size of the measured variations changes. For example, if the laser spot is focused to a diameter of 20 micrometers at the focal point and the surface moves 5 mm from the focal point the spot size will be 250 micrometers. A spot this large averages out the surface variations of interest thereby diminishing the usefulness of the sensor.

The prior art includes micro-focusing systems which attempt to solve the spot size variation problem with an automatic focusing device. The automatic focusing device moves the focusing objective lens to keep the spot focused on the surface to be measured. Micro-focusing systems can maintain a 1 micrometer spot size over a 1 mm range of up and down motion. The position of the lens is then measured to determine the position of the surface. The advantage of this system is that the spot size remains constant even when the surface moves up and down. The disadvantage of this device is that its speed is limited since the lens must be moved mechanically. Accordingly, microfocusing systems have frequency responses of only up to about 1200 Hz.

An example of a prior art on-line optical surface sensor is disclosed in U.S. Pat. No. 4,019,066 issued Apr. 19, 1977. As explained in that patent, the device illuminates the moving sheet, preferably at a low angle. Light scattered from the sheet is collected and processed by means of a photoelectric system. The electrical signals thus generated are divided into AC and DC components which are separately measured and their ratio is used as an index of roughness. Because this instrument senses the intensity of backscattered light and not spot position, it does not provide accurate results for smooth paper.

U.S. Pat. No. 4,092,068 issued May 30, 1978 discloses an on-line optical surface sensor in which, again, the intensity of light scattered from the surface of a traveling sheet is detected, in this case by two angularly spaced photodetector cells whose outputs suppress local reflectivity changes resulting from dirt or the like on the surface of the sheet. The incident light beam from an incandescent source is projected perpendicular to the surface of the sheet and illuminates a light spot having a relatively large diameter of 0.1 to 0.2 mm. This device, like that disclosed in U.S. Pat. No. 4,019,066, cannot provide accurate readings from smooth surfaces.

To measure sheet surface smoothness, attempts have also been made to use on-line gloss gauges which measure light reflected from paper. These approaches have likewise met with only partial success since paper, because of its surface properties, tends to provide both specular and non-specular (i.e., diffuse) reflections, with decreasing smoothness resulting in more diffuse reflections. Accordingly, there is often little relationship between gloss and smoothness.

Other examples of prior art non-contacting, optical systems for on-line measurement of the irregularities in the surfaces of moving sheets are disclosed in U.S. Pat. Nos. 4,102,578 and 5,110,212, and in a technical article by Schmidt, "Smoothness measurement in paper making and printing", published in Paper, 19 Apr. 1982, pages 24 et seq.

To our knowledge, none of the prior art on-line optical smoothness sensors completely satisfy all of the many requirements that must be met in order to be truly useful with today's papermaking machines. An acceptable on-line smoothness sensor must provide information that correlates well with that furnished by accepted laboratory smoothness testers, but must in addition be capable of providing accurate smoothness measurements for the smoothest printing grades. Because of the line speeds involved (which may exceed 1,200 meters per minute) and the need to resolve surface features having amplitudes and wavelengths as small as 0.1 micrometers and 20 micrometers, respectively, the incident light spot must be small, no more than about 20 micrometers in diameter, and the sensor must have an exceedingly high frequency response. The range of the sensor must be adequate to cover the complete range of the positions of the surface features of interest while at the same time preserving sensitivity to small positional variations. Because of the small amplitudes of the signals produced by the microtopography of the sheet surface, noise introduced by the sensor must be minimized in order to obtain a usable output signal. Moreover, the position of the moving sheet must be stabilized along the optical axis of the incident beam, that is, sheet "flutter" must be minimized in the region of the sensor so as to maintain the focus of the incident light spot and preserve measurement resolution. Still further, because of the vast quantity of information provided at the output of a smoothness sensor meeting the foregoing requirements, and because there are several types of printing processes each requiring different surface properties for best printing results, the information must be so processed that it can be displayed to the machine operator and used as a process control parameter in a meaningful and practical fashion. Last, provision must be made for automatic standardization of the sensor.

In sum, a need remains for an on-line instrument that will give immediate and accurate measurements, correlatable with standard laboratory test methods, of smoothness so as to be able to determine whether or not the paper being fabricated will be printable and that will provide such measurements for the smoothest printing grades. Further, paper product manufacturers need to be able to control the paper fabricating process so as to control the smoothness, and hence the printability, of the paper being made, and to do so in response to accurate on-line measurements of smoothness that are meaningful for the paper product being manufactured.

Certain macrotopographical surface features are also of interest to manufacturers of sheet material such as paper. For example, in the manufacture of tissue, creping is an important way of increasing the texture and softness of the tissue. Creping is the process of putting small folds in the tissue sheet. The depth and spacing of the folds imparts texture to the sheet. For example, tissue with large spacings between folds will feel coarser than a sheet with close spacing.

As far as can be determined, no on-line measurement of creping is currently available. Although laboratory testers exist for measuring the height and spacings of creping folds, the use of these testers is time consuming. The quality of tissue being produced is typically assessed in a subjective fashion, based on no more than the "feel" of the tissue and a visual examination thereof by an experienced operator. Based on these assessments, the flow rate of the spraybar applying adhesive to the Yankee cylinder may be adjusted and/or the creping or doctor blade which strips the tissue from the Yankee cylinder may be replaced. The doctor blades wear out quite fast, in some cases as often as once per hour. Thus, a technique for determining accurately when to change blades could result in significant savings to a mill. Changing blades too soon results in loss of production and increased blade costs. Changing blades too late results in the production of waste product.

Thus, there is a need for an on-line sensor for measuring tissue creping and using such a measurement for the control of the creping process and for the determination of blade wear and the need for blade replacement.

SUMMARY OF THE INVENTION

The surface characteristic sensor of the present invention addresses all of the problems summarized above and satisfies the competing requirements outlined. The sensor measures the smoothness of the paper surface on-line. It produces a spectrum of amplitude versus scale size of variations in the surface features. It has been determined that one or usually more of the regions of the spectrum correlate well with laboratory air leak tests. Additionally, the laboratory "Micro Average" measurement can be duplicated with the on-line sensor of the invention. The sensor of the invention has a very fast response (1 MHz), a small spot size (approximately 20 micrometer), resolves 0.1 micrometer surface contours and is substantially insensitive to flutter, that is, up and down motion, of the sheet. Further, automatic standardization is provided to verify the performance of the device for extended periods of time.

More particularly, in accordance with one particular exemplary embodiment of the present invention, there is provided an apparatus for the continuous, on-line measurement of the topographical features of a surface of a moving sheet, the features having various scale sizes and heights. The apparatus comprises a laser light source and means, including lenses, for focusing incident light from the laser source along an optical path intercepting the surface of the moving sheet to illuminate a light spot on the surface. The apparatus further includes means for collecting light scattered at a non-specular angle from the illuminated spot and for focusing an image of the spot on a photosensitive detector responsive to the position of the image. The image of the spot on the photosensitive detector provides a signal representing variations of the height position of the light spot on the surface of the moving sheet. As various surface features move past the sensor, a spectrum of frequencies is produced in response to the scale sizes of the features. Circuitry for processing the detector output signal includes at least one channel having a filter for filtering out low frequency variations in the detector output signal resulting from low frequency phenomena such as sheet flutter and passing higher frequencies in the detector output signal representing a range of surface feature scale sizes.

Preferably, the signal processing circuitry comprises a plurality of channels each including a filter, the filters having different cut-off frequencies for passing different frequency spectra representing different ranges of surface feature scale sizes. Because the frequencies of the detector output signal vary as a function of line speed, the apparatus includes means for monitoring the speed of the moving sheet and providing an output indicative the speed. The cut-off frequency of each of the filters is varied in response to variations in the output of the sheet speed monitoring means.

Preferably, the photosensitive detector comprises a segmented, balance detector comprising a pair of side-by-side photosensitive cells separated by a small linear gap. The reflected light focused on the balance detector bridges the gap so as to illuminate to a greater or a lesser extent the detector cells substantially in accordance with the height position of the light spot illuminating the surface of the moving sheet. The detector thus generates a pair of signals, the detector output signal being proportional to the difference between the signals of the pair of signals. A circuit is provided at the output of the detector for processing the pair of detector signals and providing an output that is a function of the ratio of the difference between the signals of the pair of detector output signals to the sum of those signals.

In accordance with another feature of the invention, in order to extend the range of the balance detector, the linear gap separating the balance detector cells is disposed at an angle to the direction of movement of the light spot incident on the detector.

The filter in each channel, according to one embodiment of the invention, comprises a high pass filter. In this case, the signal processing circuitry may include an arithmetic unit for selecting the outputs from two of the channels and generating a signal representative of the region of the spectrum between the selected channel cutoff frequencies. In this way, the spectrum is divided into a plurality of regions, each region providing an indication of height variations in the sheet surface within a particular scale size or wavelength range. An alternative way of providing such information is to use bandpass filters.

In accordance with another aspect of the invention, the apparatus of the invention can be provided with means for compensating for the compressibility of the sheet material. Specifically, a backing platform is positioned adjacent the surface of the sheet opposite that of the position sensor. The backing platform includes means for biasing the measurement region of the sheet illuminated by the light spot toward the bottom surface of the sensor whereby the measurement region of the paper is compressed. The biasing means may comprise an inflatable bellows having opposed end portions, one of the end portions being attached to the platform, the other of the end portions being positioned to urge the sheet toward the bottom surface of the sensor. A stabilizer arm connects the other end of the bellows to the platform, the stabilizer arm resisting the tendency of the one end of the bellows to be carried along by said moving sheet.

The apparatus of the invention also includes a standardizing member having an optical standardizing surface. With the apparatus off-sheet, the standardizing member is moved to standardizing position in which the optical standardizing surface is positioned substantially in the plane occupied by the mean surface of the sheet. There is further included means for oscillating the position of the standardizing member in a direction along the optical axis of the incident light at at least one predetermined frequency and at least one predetermined amplitude representing, respectively, at least one surface feature scale size and at least one surface feature height variation. In this way, the performance of the sensor can be verified for at least one scale size spectrum.

In accordance with another aspect of the present invention, there is provided a sheet stabilizer for use with a sensor adapted to measure a characteristic of a region of a surface of a moving sheet having opposed surfaces, the sensor being disposed adjacent one of the surfaces. The sheet stabilizer includes a guide plate attached to the sensor. The guide plate has a planar surface closely proximate to which the sheet is adapted to move, the guide plate defining a space adjacent the measurement region and a channel in communication with the space. The sheet stabilizer further includes means for supplying fluid flow along the channel, the fluid flow causing a reduction in pressure within the space whereby at least a portion of the sheet including the measurement region is biased toward the sensor. The sheet stabilizer also has a means for supplying fluid under pressure to the surface of the sheet along the measurement region of the sheet. In this fashion, a fluid bearing is defined between the planar surface of the guide plate and a bottom surface of the sensor and the measurement region of the sheet is maintained at a precise vertical location relative to the sensor.

Many steps in a typical papermaking process are devoted to achieving surface smoothness. Numerous control arrangements are made possible by virtue of the surface sensor of the invention. The specific aspects of the fabrication process that are controlled depends on the particular type of paper product being made. In accordance with another aspect of the invention, there are provided strategies for controlling various papermaking process parameters that determine the smoothness of the final product.

The present invention can also be used to measure macrotopographical features such as tissue creping. The sensor produces a spectrum of amplitude versus scale size of folds in the tissue. Coarse tissues have peak amplitudes at larger scale sizes than smooth tissues. With this quantitative measure of creping available on-line, automatic control of the process can be implemented. Further, optimum blade change intervals can be determined.

BRIEF DESCRIPTION OF THE DRAWINGS

Other objects, advantages and features of the present invention will become apparent from the detailed description, below, when read in conjunction with the accompanying drawings in which.

DETAILED DESCRIPTION OF THE PREFERRED EMBODIMENTS

Optical Position Sensor

Figure 1:
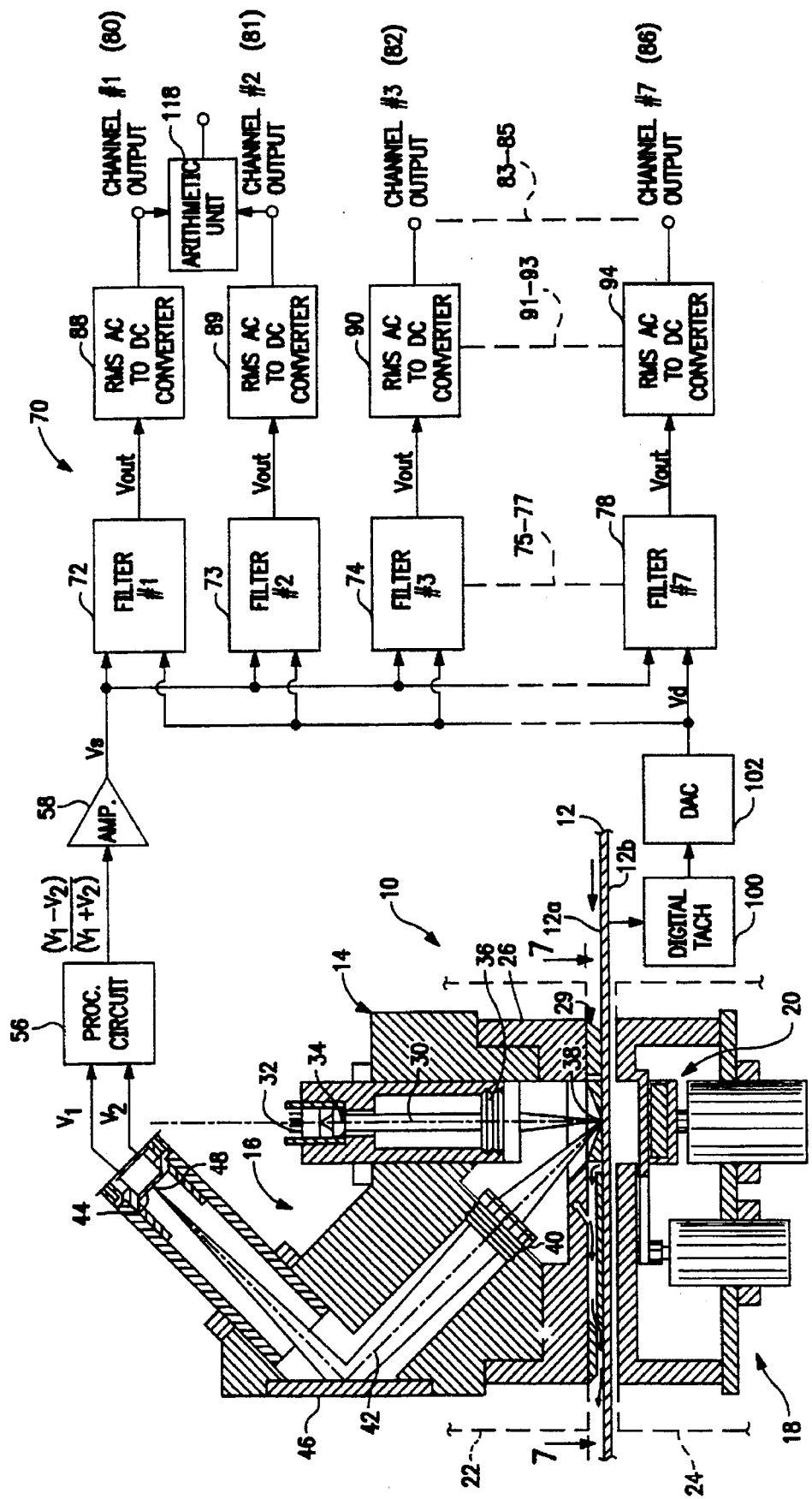
FIG. 1 is a schematic diagram of an apparatus for measuring surface characteristics of a traveling sheet of paper, in accordance with a preferred embodiment of the present invention.

Referring to FIG. 1, there is shown an optical sensor 10 for measuring the surface characteristics of a sheet of paper 12 traveling past the sensor toward a wind-up roll (not shown) in the direction indicated by the arrows. The paper sheet 12 has top and bottom surfaces 12a and 12b, respectively. The sensor 10 comprises two main assemblies: an upper assembly 14 containing the elements of a laser triangulation optical position sensing system 16 and a lower assembly 18 carrying means 20 for standardizing the sensor. The upper assembly 14 is mounted in the upper head 22 (the outline of which is shown by broken lines) of a conventional scanner while the lower assembly 18 is carried by the lower head 24 (shown also by broken lines) of the scanner. In a manner well known in the art, the upper and lower heads 22 and 24 travel back and forth in unison across the width of the sheet 12 in the "cross direction", that is, in a direction transverse to the direction of travel of the sheet 12, also called the "machine direction".

In the embodiment shown in FIG. 1, the features of the top surface 12a of the sheet 12 are measured. It will be evident, however, that the laser triangulation position sensor 16 may be mounted in the lower head 24 and the standardization means 20 may be mounted in the upper head 22 to measure the surface characteristics of the bottom surface 12b of the sheet. Still further, the characteristics of both top and bottom surfaces 12a and 12b may be measured simultaneously by mounting a laser triangulation position sensor 16 in each of the scanner heads 22 and 24 and associated standardization means 20 in the opposite heads.

Figure 8:
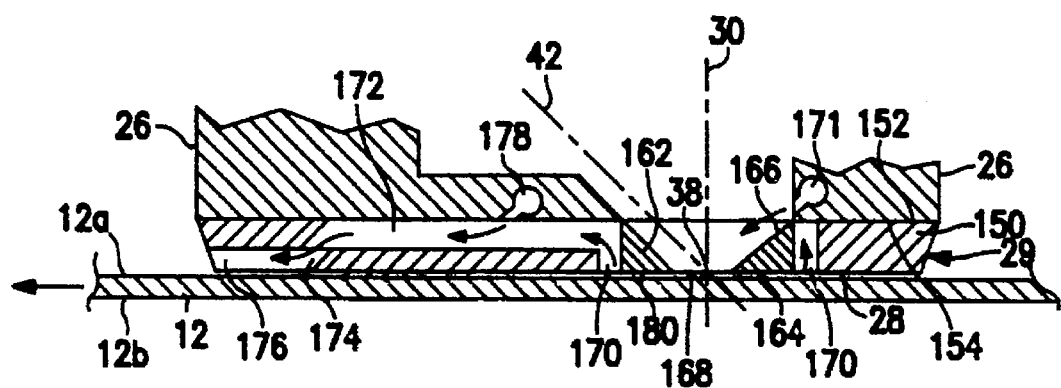
FIG. 8 is a side elevation view, in cross section, of the sheet stabilizer member of FIG. 7 as seen along the section line 8—8 in FIG. 7.

With reference now also to FIG. 8, the upper assembly 14 includes a housing 26 and a bottom, horizontal reference surface 28. The upper surface 12a is stabilized along a passline relative to the reference surface 28 by means of a sheet stabilizer 29 whose details will be described below, so as to minimize "flutter", that is, vertical motion or displacement of the sheet 12 from the passline as it moves past the sensor. The sheet stabilizer 29 is effective to constrain vertical displacement of the sheet so that flutter is limited to about ±0.1 mm about the mean passline.

The laser triangulation optical sensing system 16 housed in the upper assembly 14 includes, along a vertical beam axis 30 intersecting the plane of the bottom reference surface 28, a laser beam source 32, which may take the form of a laser diode, an aspheric collimator lens 34 and an objective lens 36. The lens 36 focuses the laser beam onto a tiny spot 38 on the sheet surface 12a. The diameter of the light spot 38 is selected depending upon the resolution desired. For example, if the smallest scale size or wavelength of the surface variations of interest is taken as that of the dot spacing of a half tone printing plate, that is, about 20 micrometers, the diameter of the light spot 38 should be no more than about 20 micrometers. In the embodiment of the invention shown in FIG. 1, the beam axis is perpendicular to the surface 28; it will be evident, however, that the beam axis 30 may be oriented at other angles relative to the surface 28.

Figure 2:
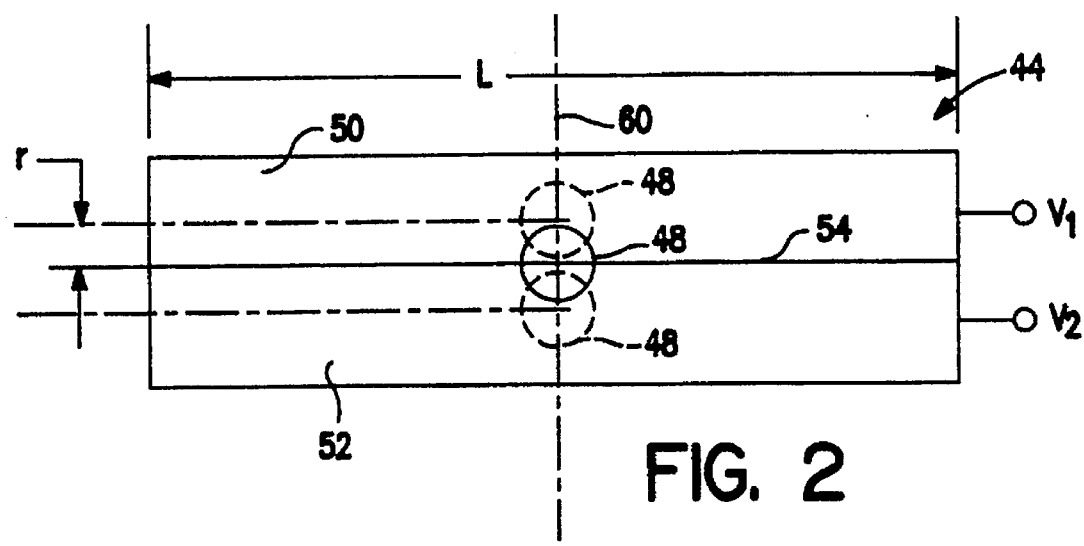
FIG. 2 is a front view of a segmented balance photodetector of the type that may be used in the apparatus of FIG. 1.
Figure 3:
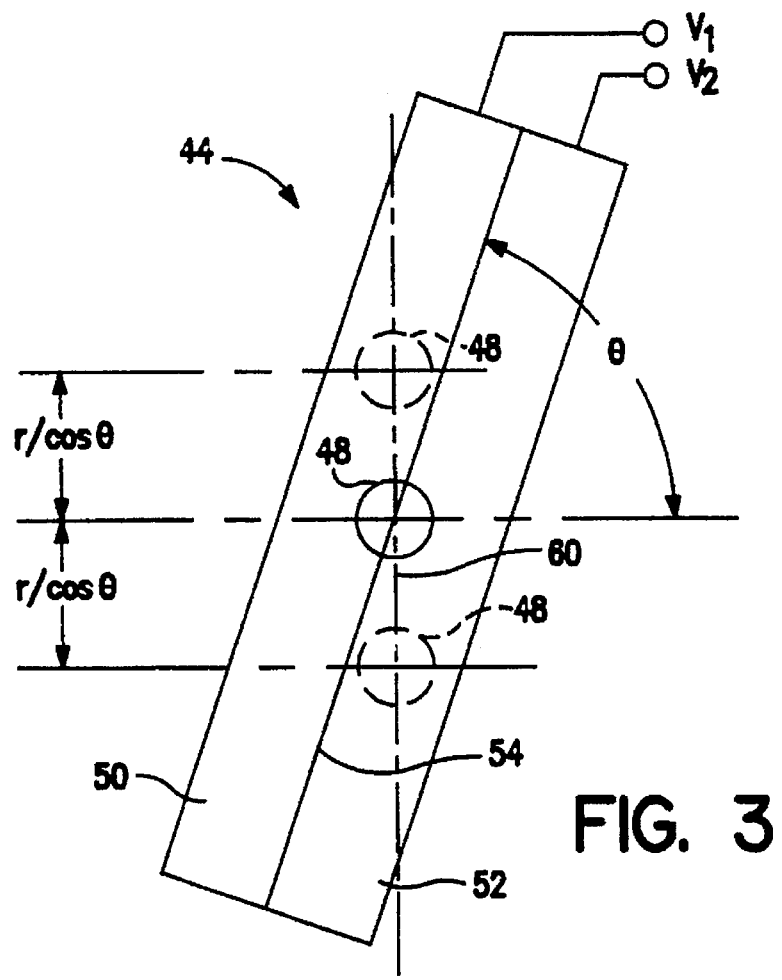
FIG. 3 is a front view of the balance detector of FIG. 2 showing the extended range orientation in which it is used in the apparatus of FIG. 1.

Light scattered from the illuminated spot 38 on the top surface 12a of the paper sheet is collected and focused by an objective lens 40 along a reflected beam axis 42 at 45° to the incident beam axis 30, onto a detector 44 via an adjustable mirror 46. Because of the nature and size ranges of the surface features whose positions, i.e., heights, are sought to be measured, the detector 44 must satisfy certain stringent requirements. Among other things, it must have a high frequency response, a high signal-to-noise ratio and a sufficient height position range to accommodate vertical sheet displacements relative to the reference surface 28. FIGS. 2 and 3 show details of a segmented balance detector 44 meeting these requirements. The focused beam reflected from the mirror 46 illuminates a small area 48 which overlaps to a greater or lesser extent the receiving surfaces of a pair of side-by-side, rectangular photodetector cells 50 and 52 separated by a linear gap 54 having a width, for example, of 20 micrometers. A balance detector of this kind, also called a BiCell, is sold by Silicon Detector Corp., Camarillo, Calif., U.S.A. These are low noise detectors having high frequency responses of the order several MHz and greater, exceeding substantially the responses of CCD-type and lateral cell position sensitive detectors traditionally used in laser triangulation position sensors.

The photodetector cell 50 provides a voltage output V1 proportional to the extent to which it is illuminated by the light spot 48; in a similar fashion, the cell 52 produces a voltage output V2. The outputs V1 and V2 are applied to a processing circuit 56 which generates a surface position signal that is the ratio of the difference between V1 and V2 to the sum of these signals $[(V1-V2)/(V+V2)]$. Thus, the position output signal is proportional to the difference between the voltage outputs of the cells, i.e., the difference in the illumination of the cells 50 and 52, while being compensated for variations in the intensity of the reflected light. The ratio signal is fed to an amplifier 58 to provide an amplified position signal, Vs. It will be seen that when the light spot illuminates a portion of the top surface 12a of the sheet 12 that is at the ideal or mean plane of the top surface, the light spot 48 will be centered on the cells 50 and 52 of the balance detector 44 and Vs will equal zero. The adjustable mirror 46 may be tilted about an axis perpendicular to the plane of the drawing of FIG. 1 so as to center the reflected light spot 48 on the balance detector when the incident light spot 38 is at the ideal plane of the surface 12a, thereby mechanically zeroing the sensor. Thus, the mirror 46 is adjusted so that when sheet surface 12a is in the middle of the range of its vertical displacement, the image of the light spot 48 is focused so that the detector cells 50 and 52 are equally illuminated. When the height, i.e., the vertical position of the sheet surface 12a varies, the spot image 48 moves so that one cell receives more light than the other. When the balance detector 44 is used in its usual orientation, shown in FIG. 2, the axis of the gap 54 is perpendicular to the direction 60 of spot image motion and the range of the sensor is equal to the radius, r, of the light spot 38. This limit is unaffected by the magnification imparted by the lens along the optical path. Thus, for an incident light spot 38 having a diameter of 20 micrometers, the range of position variations would be ±10 micrometers. To accommodate a maximum sheet flutter range of ±0.1 mm, for example, the balance detector 44 is used in a new way. As shown in FIG. 3, the detector 44 has been reoriented, with the linear detector gap 54 rotated through an angle θ. With the detector so oriented, its range is increased to r/cosθ. The maximum range depends on the overall length, L, of the detector and the magnification, M, of the optics; thus, the maximum range=±L/2(M). The magnification is determined by the optical design and can be virtually any number desired. However, as the range designed into the system increases, the sensitivity to small variations in position decreases. The minimum sensitivity is determined by the smallest variations that must be detected and the noise level of the detector. For example, if the balance detector 44 has an overall length, L, of 4.88 mm and the magnification, M, along the reflected path is 23, the maximum range is ±0.106 mm.

The amplified detector output signal, Vs, comprises a varying signal whose amplitude varies in accordance with the height or vertical position of the portion of the surface 12a illuminated by the incident light spot 38 and whose frequency varies in accordance with the scale sizes or wavelengths of the observed features and with the local line speed, i.e., the speed of the paper as it moves past the sensor. Thus, Vs contains a frequency spectrum that, for a given line speed, contains all of the frequencies associated with the entire range of micro- and macrotopographical scale sizes.

When the surface 12a of the sheet 12 moves up and down relative to the reference surface 28, the image of the light spot 48 on the detector will move and the detector output will change accordingly. The detector output will indicate a surface position which includes both flutter and surface contours. For smoothness, only the surface contours with scale sizes from 20 micrometers to about 1 mm are of principal interest. For a sheet moving at 1,200 meters/min these scale sizes translate to frequencies ranging from 1 MHz to 20 kHz. (The sensor will work on machines having line speeds greater than 1,200 meters/minute, but the smallest scale size that can be resolved will increase proportionately with speed.) The flutter variations will occur at substantially lower frequencies, for example, a few hundred Hz. To measure the microtopographical surface features associated with smoothness only the high frequency signal components corresponding to smoothness scale sizes of interest (e.g., 20 micrometers to 1 mm) need to be used.

Signal Processing Circuitry

With further reference to FIG. 1, the amplified position signal, Vs, is fed to signal processing circuitry 70 which processes the amplified position signal, Vs, to provide electrical output signals indicative of the heights of sheet surface features for a predetermined range or ranges of scale sizes or wavelengths. The signal processing circuitry 70 includes at least one, and preferably a plurality of filters 72–78 (of which only filters 72–74 and 78 are shown) to which are applied the signal Vs. Each filter 72–78 is associated with a particular electrical "channel" 80–86, respectively. Besides one of the filters 72–78, each channel 80–86 includes an RMS-AC to DC converter 88–94, respectively, connected to the output of the filter associated with that channel. The amplitude of the voltage output from each RMS converter 88–94 is directly proportional to the height of the surface variations for the scale size or wavelength range covered by the particular channel. The processing circuitry 70 may have any number of channels. In the embodiment of FIG. 1, the circuitry has seven (7) channels covering a total frequency range spectrum selected according to the total range or spectrum of scale sizes (wavelengths) of interest.

In accordance with one embodiment of the invention, each of the filters 72–78 may comprise a high pass filter having a cutoff frequency different than those of the other filters and selected in accordance with the scale size (wavelength) range or spectrum to be covered by the channel with which the particular filter is associated. As already noted, the frequency of the output signal, Vs, varies with line speed. Accordingly, the cutoff frequency of each filter must be adjusted for line speed changes so that the scale size range or spectrum covered by each channel remains constant even when there is a change in the speed with which the paper sheet 12 passes the sensor 10. The line speed is measured by a digital tachometer 100 which may be mounted on the take-up reel (not shown) of the papermaking machine. Connected to the output of the digital tachometer 100 is a digital-to-analog converter (DAC) 102 which generates an output control voltage, Vd, proportional to the tachometer counts. The signal Vd is applied to each filter 72–78 to adjust the cutoff frequency as required.

The cutoff frequency of the high pass filter 72 of the first channel 80 is highest; this would therefore comprise the "fastest" channel responsive to height variations having the smallest scale sizes ranging from 20 micrometers (the smallest size that can be resolved) to the wavelength corresponding to the highest cutoff frequency. The second channel 81 would provide an output proportional to surface feature heights having a wavelength range from 20 micrometers to that corresponding to the cutoff of high pass filter 73 which cutoff is somewhat lower than the cutoff of filter 72; and so forth. Each channel, then, provides height or position information concerning a predetermined spectrum of surface features. In this fashion, the large volume of information produced by the detector 44 is broken down into a form in which it can be readily displayed (for example, by way of a bar graph with each bar representing the output of one of the channels) and understood by the mill operator. The total frequency spectrum covered by the various channels and the division of that spectrum among the channels can be preselected depending upon the surface characteristics of the paper products to be produced. For example, the overall frequency range can be compressed to 20 micrometers to 1 mm, the scale size range of most interest to the determination of paper smoothness. Alternatively, the total spectrum can be expanded to include spectra extending to the macrotopographical features of the sheet surface. For example, the seven channels can have cutoffs corresponding to the following scale sizes, in micrometers: 125; 250; 500; 1,000; 2,000; 4,000; and 8,000.

Figure 4:
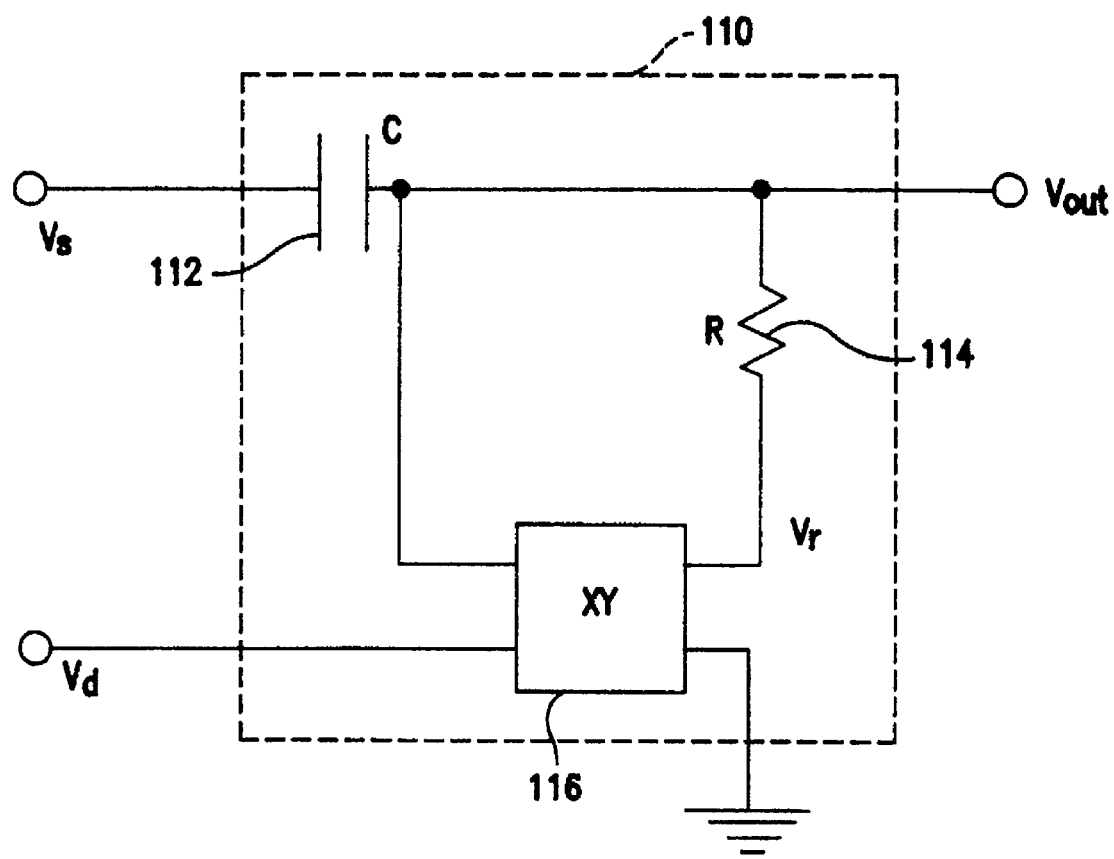
FIG. 4 is a schematic diagram of a controlled cutoff frequency, high pass filter which may be used in the apparatus of FIG. 1.

FIG. 4 shows a variable cutoff frequency high pass filter 110 that may be used in the signal processing circuit 70. The filter 110 is basically an RC circuit including a capacitor 112 (C) and a fixed resistor 114 (R). The filter 110 further includes an XY multiplier 116 functioning as a voltage controlled resistor, Rx, in series with the fixed resistor 114 and across which a voltage, Vr, appears. The inputs to the multiplier 116, i.e., the quantities multiplied by the circuit 116, comprise the speed signal, Vd, and the output voltage, Vout.

The cutoff frequency, as a function of line speed, for the high pass filter circuit 110, may be derived as follows:

The cutoff frequency, fc, of a high pass RC filter is:

$$fc = 1/(2\pi * Rt * C)$$

where Rt is the total resistance from Vout to ground. In the circuit 110:

$$Vr = Vd * Vout$$

$$Vr = Vout * (Rx/(R+Rx))$$

Combining the two equations:

$$Vd * Vout = Vout * (Rx/(R+Rx))$$

This reduces to:

$$Vd * (R+Rx) = Rx$$

Solving for Rx yields:

$$Rx = R * Vd/(1-Vd)$$

The total resistance, Rt, from output to ground is:

$$Rt = R + Rx = R * (1 + Vd/(1-Vd))$$

Finally:

$$Rt = R/(1-Vd)$$

and:

$$fc = (1-Vd)/(2\pi * R * C)$$

Thus, the cutoff frequency, fc, of the filter 110 is a function of the line speed signal, Vd.

The high pass filter 110, which is a simple one-pole filter, performs well to 1 MHz. In a manner known in the passive filter art, a plurality of filters 110 can be cascaded to form multipole filters having somewhat sharper frequency cutoff characteristics.

As already discussed, the processing circuit 70 includes an array of seven filters in parallel for dividing the spectrum into seven regions. By way of example, the fixed resistor, R, of each successive filter may be larger by a factor of two (2) than the fixed resistor of the previous filter, defining a cutoff frequency, fc, that is an octave lower. When Vd is zero, the cutoff frequencies are maximum, corresponding to maximum line speed. As the line speed is reduced, Vd is increased, causing a linear decrease in fc in proportion to line speed.

In certain situations, the mill operator will want to know the magnitude of height variations in the sheet surface within a particular scale size or wavelength range. The apparatus of the present invention can provide this information by simply taking the square root of the difference between the RMS DC output of one channel squared and the RMS DC output of another channel squared. The value obtained corresponds to the magnitude of the height variations within the scale size range between the cutoff frequencies of the high pass filters of the two channels. An arithmetic unit can be provided for this purpose. For example, in FIG. 1 an arithmetic unit 118 is shown connected to the output terminals of channels 80 and 81. The output of the arithmetic unit 118 corresponds to the magnitude of the surface height variations within the scale size range between the cutoff frequencies of the high pass filters 72 and 73.

If the outputs of the various channels are numerically displayed, then the paper mill operator can obtain the results between any two such outputs numerically. For example, to determine the magnitude of the height variations having wavelengths between 125 and 250 micrometers, the paper mill operator simply subtracts in quadrature the value of the output of the second channel from the value of the output of the first channel.

Figure 5:
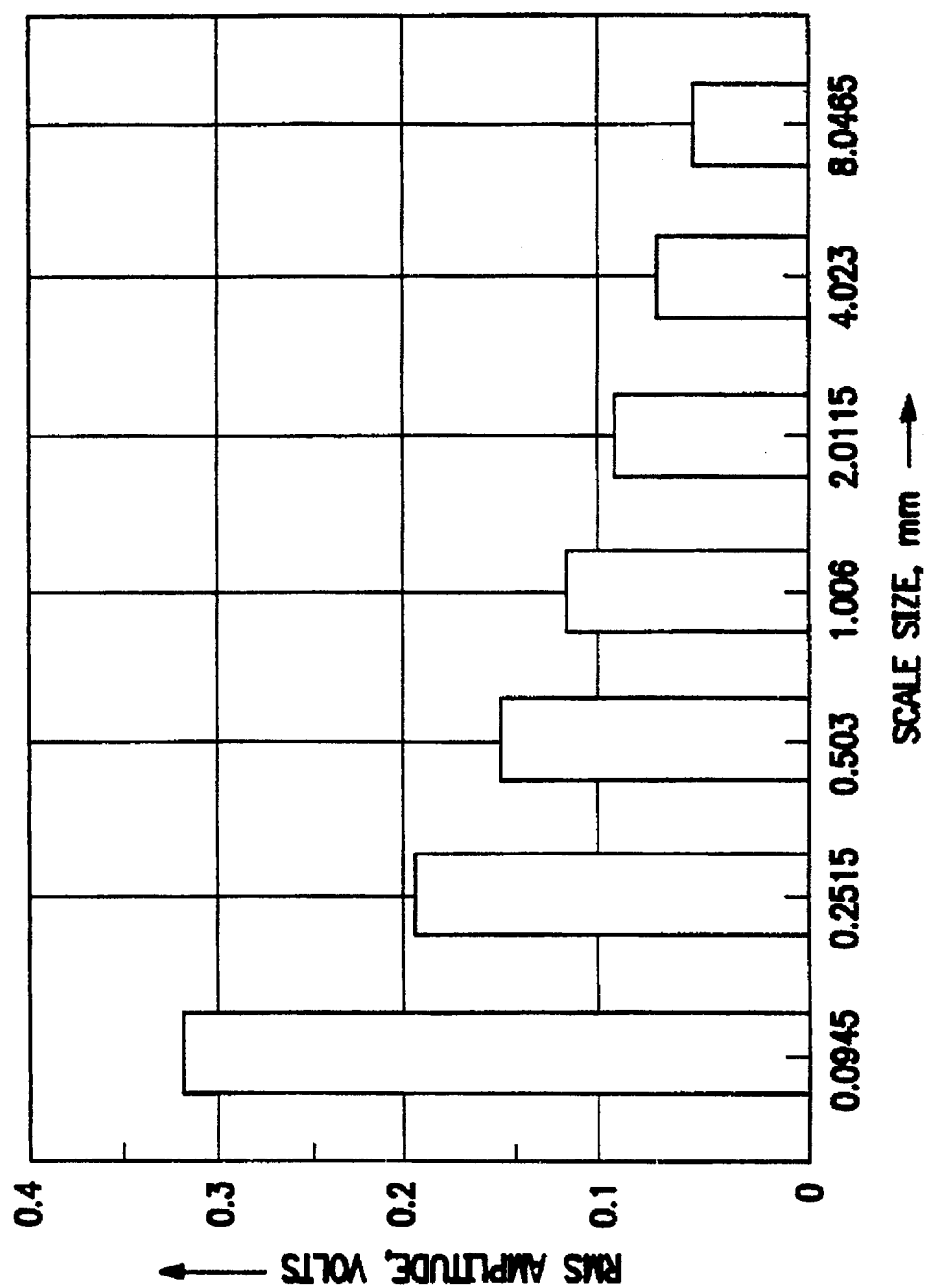
FIG. 5 is a graphical representation of the outputs of the various channels of the apparatus of FIG. 1 for a typical, relatively smooth paper.

It will be obvious to those skilled in the art that instead of high pass filters, low pass filters can be used instead. Still further, bandpass filters combining high and low pass filters can be employed in which case the high frequency cut-off value of each bandpass filter would be set equal to the low frequency cut-off value of the preceding filter. As a result, where seven channels are utilized, the seven bandpass channels would provide surface height information for seven contiguous, nonoverlapping frequency spectra corresponding to seven contiguous scale size or wavelength ranges. FIG. 5 shows how such information may be presented on the display of a computer programmed to process the data produced by the channels 80–86.

FIG. 5 is a representation of a graphical display of the surface sensor channel outputs along the lines of what might be expected for a typical, rotogravure grade glossy paper. Such paper is very smooth. The bar graph of FIG. 5 is for a surface sensor incorporating bandpass filters in its signal processing circuitry. Each of the seven scale sizes shown along the X axis of the graph of FIG. 5 is the scale size corresponding to the middle of the bandpass filter frequency range used for that channel. The voltage output of each channel (the Y axis) is the RMS voltage amplitude of the surface contours in each scale size (wavelength) region. The voltage is directly proportional to the height of the surface variations. Thus, in the graphical representation of FIG. 5, with one volt representing approximately 15 micrometers of surface height variation, the height of the surface variations measured by the channel covering the largest scale sizes is about 0.8 micrometers while the height of the surface variations measured by the channel covering the smallest scale sizes is 4.5 micrometers. The channel output pattern shown in FIG. 5 is characteristic of very smooth paper since most of the height variations are seen in the first two or three channels covering the surface features having the smallest scale sizes.

The ratio signal from the sensor gives deviations of small scale surface variations from the mean surface position. The signal can be used to develop a statistical distribution of the deviations. Properties of the distribution such as standard deviation, skewness and keratosis can be calculated. The correlation length of the autocorrelation function can also be calculated. These parameters characterize the surface smoothness of the sheet and can be correlated to other smoothness measurements such as Parker Print Surf (PPS).

It should be noted that many standard "RMS" AC-to-DC converters actually measure the peak-to-peak voltage of the incoming signal and then provide an output DC signal which corresponds to the "true" RMS value of the input signal only if the input signal is sinusoidal. However, the amplified detector output, Vs, applied to the filters 72–78 in FIG. 1 has a wave shape that is typically not sinusoidal. It is therefore usually important that the AC-to-DC converters 88–94 provide DC output voltages corresponding to the true RMS value of the detector output signal, otherwise the output signal of these RMS converters may provide an inaccurate measure of the height variations.

The use of true RMS-AC-to-DC converters is particularly important when the output of the converter of one channel is "subtracted" from the output of a converter of another channel to thereby determine the surface roughness heights within a particular scale size or wavelength range. Different wavelengths may cause the same peak-to-peak changes in the height signal even though their contribution to the RMS value of the height signal is different. Thus, if the "RMS" signal is actually derived from a measurement of the peak-to-peak signal value and signals having different wavelengths have the same peak-to-peak change in Vs, then the difference between the outputs of two "RMS" converters would be zero, which would be incorrect. Thus, the use of standard peak-to-peak AC-to-DC converters may give false readings when used in the device of the present invention and it is important that "true" RMS AC-to-DC converters be used.

The "Micro Average" explained earlier is calculated by measuring the height of the surface 12a of the sheet 12 at successive, uniformly spaced apart points along the sheet. For example, the spacing between successive measurement points may be 0.005 inch. As already stated, the "Micro Average" is the average of the absolute value of the differences between successive height readings over the entire set of readings. Since the laser surface sensor of the present invention measures the heights of the surface smoothness features on a moving sheet, it can be used to provide successive height measurements along the surface from which the "Micro Average" can be calculated. A digital circuit for providing the "Micro Average" automatically on-line for purposes of display and/or process control is shown in FIG. 6.

Figure 6:
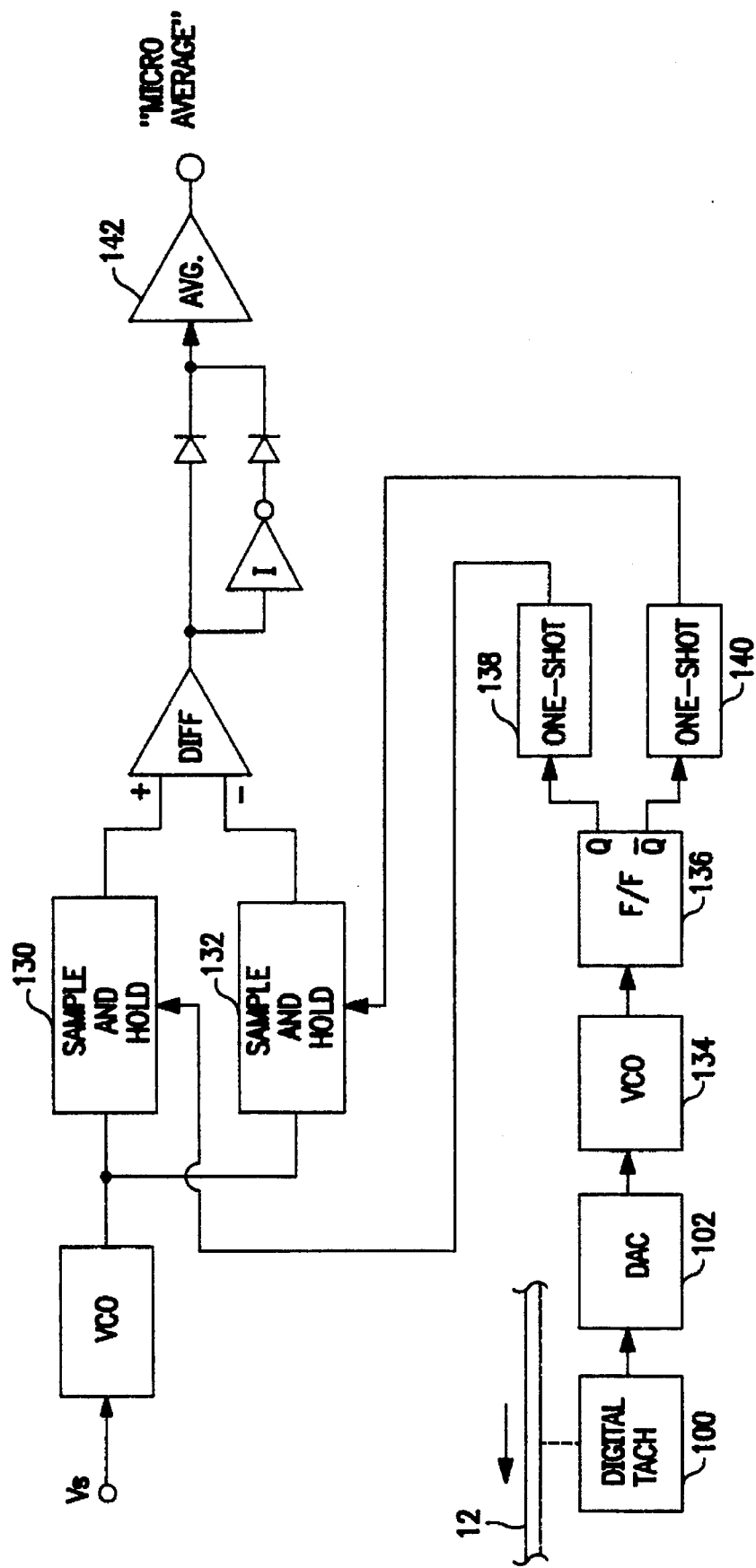
FIG. 6 is a schematic diagram of a circuit which may be used with the apparatus of FIG. 1 for calculating the "Micro Average" of the measurements made by the apparatus.

The circuit of FIG. 6 includes two fast sample and hold amplifiers 130 and 132 which receive as an input signal the amplified detector signal, Vs. The sample and hold circuits 130 and 132 are timed to alternately update on the input signal and to store successive data samples. Timing is controlled by a voltage controlled oscillator (VCO) 134 which is adjusted according to a signal proportional to line speed. The output pulses from the VCO control a flip-flop 136 whose Q and Q outputs are connected to a pair of one-shots 138 and 140 which in turn are coupled to the sample and hold circuits 130 and 132. The one-shots 138 and 140 establish a predetermined time period during which the sample and hold circuits 130 and 132 are enabled to acquire data. The beginning of each data acquisition interval is timed by circuit elements 100, 102, 134 and 136, however, so as to be synchronized to line speed. The difference between the outputs of the two sample and hold amplifiers is averaged by an averaging circuit 142 to yield a running value of the "Micro Average".

Sheet Stabilization

Figure 7:
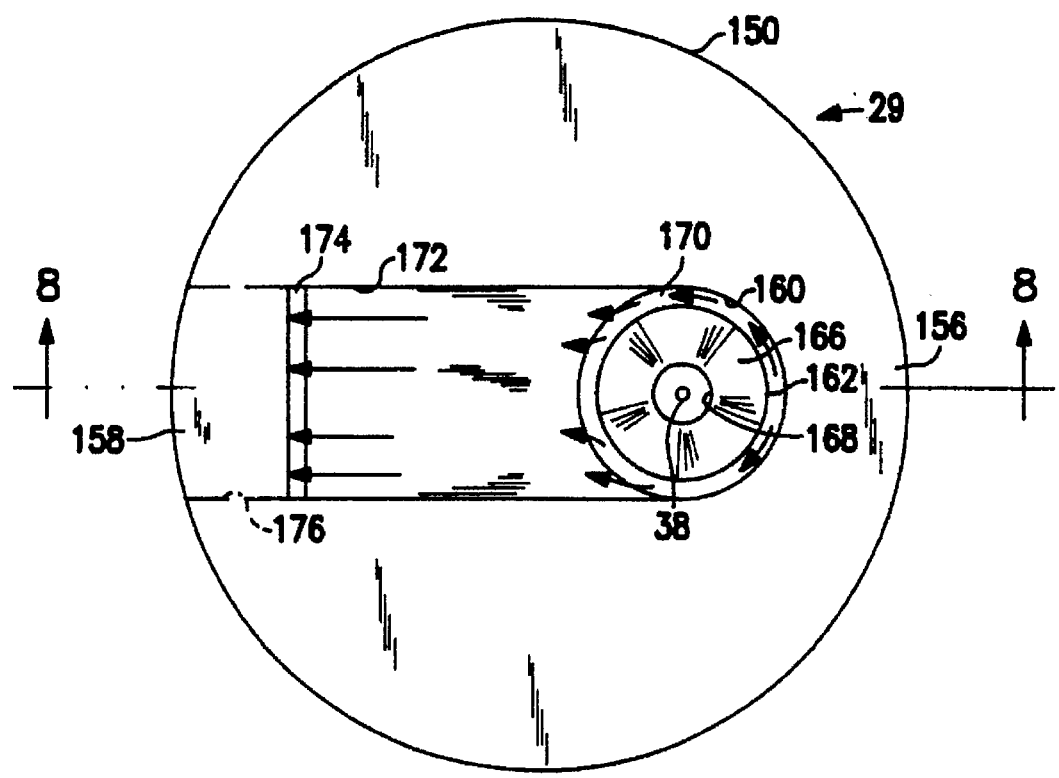
FIG. 7 is a top plan view, as seen along the section line 7—7 in FIG. 1, of a sheet stabilizer member forming part of the sensor of the invention.

With reference to FIGS. 7 and 8, there is shown in greater detail the sheet stabilizer 29 which is secured to the bottom of the sensor housing 26. The sheet stabilizer 29 is effective to minimize sheet flutter in the vicinity of the region of the measurement spot 38 and to stabilize the vertical position of the sheet 12 along a mean sheet passline. The stabilizer 29 can maintain the top sheet surface 12a within a ±0.1 mm range of its mean position. The sheet stabilizer 29 includes a sheet guide 150 in the form of a circular plate having an upper surface 152 and a lower surface 154 defining the reference surface 28 adapted to be engaged by the upper surface 12a of the moving sheet 12. The plane of the reference surface contains the focus spot 38 of the incident beam optics. The guide 150 includes a first or upstream end 156 and a second or downstream end 158. The guide 150 defines a circular opening 160 extending through the thickness of the guide plate 150 and centered on the incident laser beam axis 30. Disposed concentrically within the opening 160 is a generally cylindrical sheet guide ring 162 having a lower flat surface 164 lying in the plane of the reference surface 28 and a generally conical interior wall 166 converging to a circular aperture 168 at the reference surface and which is coaxial with the beam axis 30. The angle of the conical interior wall 166 is such as to preclude interference between the guide ring 162 and scattered light reflected from the light spot 38. The outer diameter of the sheet guide ring 162 is smaller than the diameter of the opening 160 so that the wall of the opening 160 and the outer cylindrical surface of the sheet guide ring 162 define between them an annular space 170. Both the guide plate 150 and the guide ring 162 are secured to the underside of the housing 26 by screws or the like (not shown). The housing 26 defines an air discharge port 171 for directing air under pressure from a source (not shown) toward the aperture 168.

Formed in the upper surface of the guide plate 150 is a first, generally rectangular channel 172 extending along the machine direction. The upstream end of the channel 172 is in communication with the annular space 170 while the downstream or discharge end of the channel 174 is in communication, via a slit-like air discharge port 174, with a second, generally rectangular channel 176 in alignment with the first channel 172 and formed in the lower surface 154 of the guide plate 150. The housing 26 defines a slit 178 extending across the width of the channel 172 and which is connected to a source (not shown) of pressurized air. The slit 178 is in communication with the upper channel 172 and is oriented at an acute angle to the longitudinal direction of that channel so that air discharged from the slit 178 is directed rearwardly, that is, toward the discharge port 174. For best results, the slit should be located so as to discharge air in the upstream half of the channel 172; in the embodiment shown, air is discharged at a point about 25% of the distance from the front to the rear of the channel 172. The slit 178 is dimensioned so as to provide a high speed, low volume air flow within the channel 172. By virtue of that air flow, an ejector effect is produced, reducing the pressure within the annular space 170 (which is in communication with the channel 172) below ambient, so as to cause a low volume flow of air from the aperture 168 (which is supplied by positively pressurized air from the port 171) radially outwardly along the flat lower surface 164 of the guide ring toward the annular space 170. The air flowing along the surface 164 creates an air bearing or pad along which the top surface 12a of the sheet passes. In this way, a stable, substantially constant gap 180 is maintained between the surface 164 and the top surface 12a of the sheet 12. Depending on such factors as the paper product being processed, the pressure of the air supplied from the port 171 with the confines of the guide ring 162, the speed of the sheet, and so forth, the gap may have a thickness of about 25 to about 100 micrometers. This gap (which for a given set of conditions is substantially constant) establishes the mean passline of the sheet 12. It will also be seen that the air issuing from the port 171 tends to purge the space between the guide ring surface 164 and the top sheet surface 12a of dirt and debris and helps prevent such contaminants from entering the housing 26 through the aperture 168. Moreover, the sheet stabilizer of the invention is effective irrespective of the direction of sheet travel relative to the sensor 10.

Standardization

Figure 9:
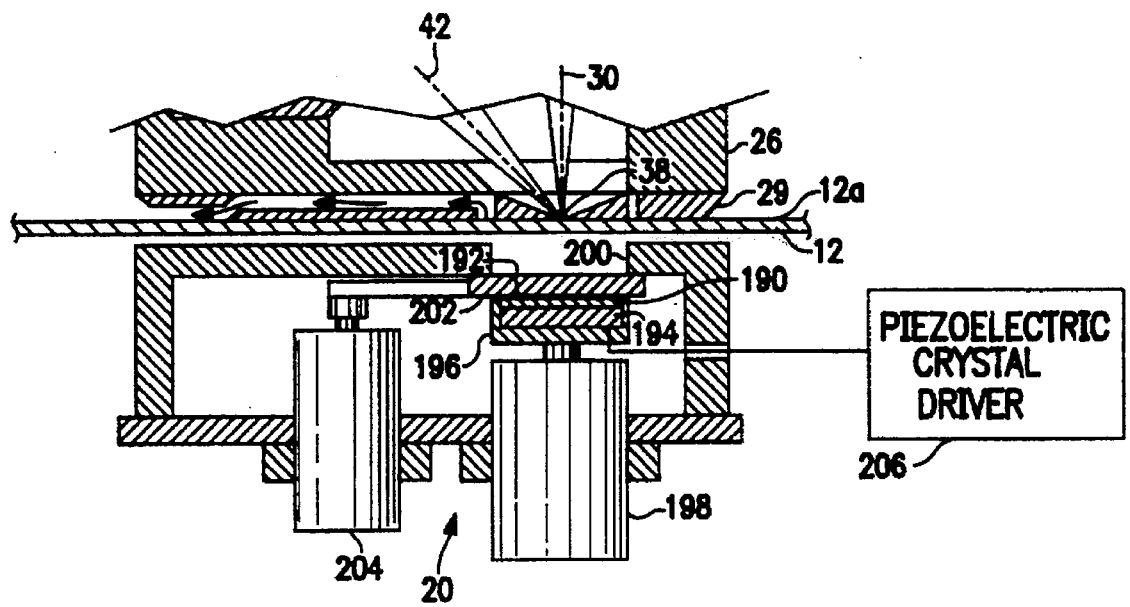
FIG. 9 is a side elevation view of a standardization device forming part of the sensor of FIG. 1, with the standardization device shown in its on-sheet position.
Figure 10:
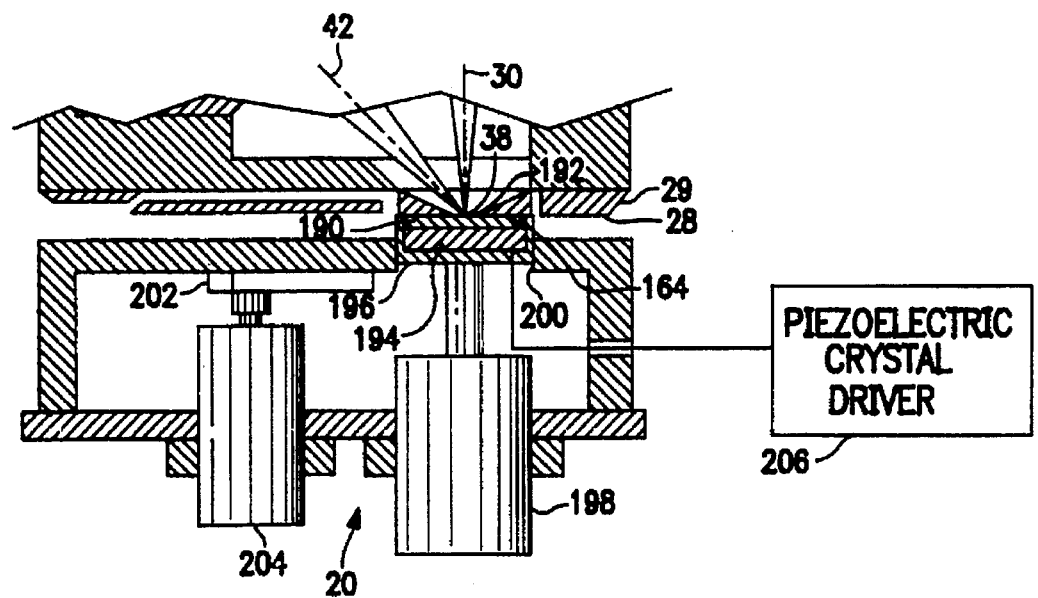
FIG. 10 is a side elevation view of the standardization device of FIG. 9 showing the device in its off-sheet, standardizing position.

With reference now to FIGS. 9 and 10, details are shown of the standardization means 20 which insures the long term stability and accuracy of the sensor. The standardization device 20 includes a ceramic disk 190 having a flat upper surface 192. The disk 190 is bonded to a piezoelectric crystal 194, and the assembly comprising the disk 190 and crystal 194 is carried by a cup-shaped housing 196 mounted on the shaft of a linear solenoid 198. The linear solenoid 198 is operative to move the housing 196 between a retracted on-sheet position (FIG. 9) and an extended off-sheet position (FIG. 10) through an opening 200 in the enclosure of the lower assembly 16. When the sensor is on-sheet (FIG. 9), the housing 196 is in its retracted position within the enclosure of the lower assembly 18 and in that position is protected from dirt, debris and moisture by a shutter 202 blocking the opening 200. The shutter 202 is movable between the opening blocking position and an unblocking position (FIG. 10) by means of a rotary solenoid 204. When the sensor is moved off-sheet (FIG. 10) by the scanner, the standardize operation can occur. The shutter 202 is first rotated to unblock the opening 200. Next, the linear solenoid 198 is energized to move the disk 190 into position against the lower surface 164 of the sheet guide ring 162. In this position the balance and the background noise level of the balance detector 44 can be measured and adjusted if necessary. Moreover, the high frequency components of the detector ratio signal, Vs, which components characterize smoothness measurements, can be simulated in accordance with another aspect of the invention by means of the piezoelectric crystal 194. For example, the crystal may be excited by a crystal driver circuit 206 at a frequency above the cut-off of the first channel high pass filter 72 to provide a measurable signal to the sensor to use as a standard of performance. Alternatively, the crystal 194 may be excited by the driver 206 at various predetermined frequencies to simulate measured surface characteristic signals within the ranges of the various channels 80–86 so that the performance of the sensor can be verified for the corresponding scale size spectra. When the standardization operation is complete, the linear solenoid 198 is energized to retract the ceramic disk 190 and the shutter 202 is rotated to close the opening 200 to protect the disk 190 from dirt and moisture.

Compressibility Compensation

Typically, laboratory smoothness testers compress the test sample to varying degrees while measurements are made. For example, the Parker Print Surf Tester applies a force of 10 kg to the sheet during performance of the air leak test while the Bendtsen tester uses 1 kg. On some paper grades, such as rotogravure, the surface is purposely made very compressible. On those grades, the surface sensor of the present invention may provide an output indicating a rough surface while a laboratory air leak tester might indicate the presence of a smooth surface.

In accordance with another aspect of the present invention, better agreement is achieved between the readings of the surface sensor of the invention and those of laboratory air leak testers by making the on-line surface measurements while pressure is applied to the sheet. In accordance with an alternative embodiment of the invention shown in FIG. 11, a laser triangulation positioning sensor system 16, of the kind already described in connection with FIG. 1, is used to measure the surface features of a moving sheet 250 traveling in the direction shown in FIG. 11, that is, from left to right. The upper surface 250a of the sheet 250 moves along the lower horizontal surface 28 of the sheet stabilizer 29, in the fashion already described. As before, the system 16 is carried by the upper head 22 of a conventional scanner.

Figure 11:
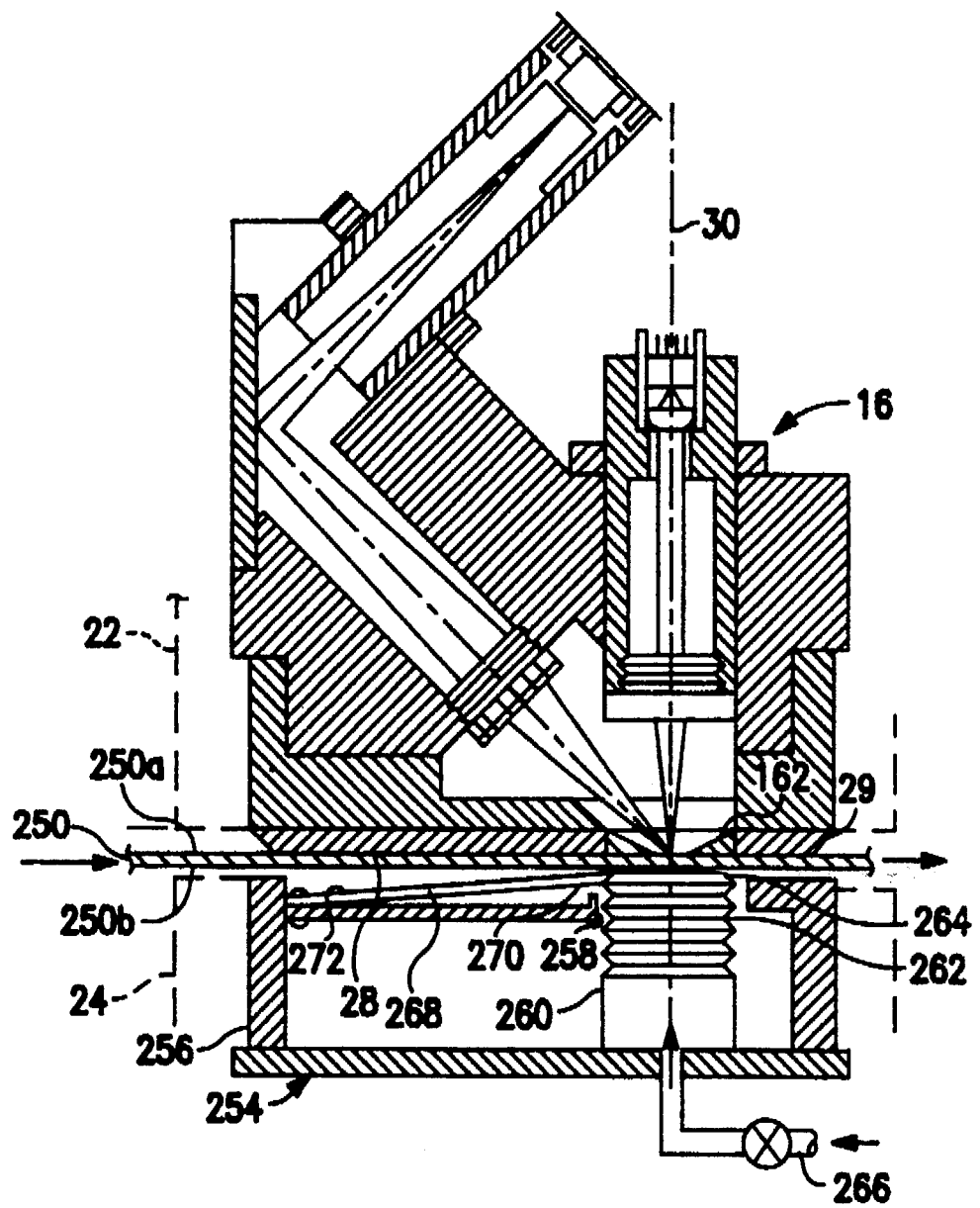
FIG. 11 is a side elevation view of an apparatus for measuring surface characteristics of a traveling sheet in accordance with an alternative embodiment of the invention providing compensation for the compressibility of the sheet.

The apparatus of FIG. 11 includes, below the sheet 250, a platform 254 mounted in the lower head 24 of the scanner. The platform 254 includes a housing 256 with an upper opening 258 in alignment with the vertical beam axis 30 of sensor system 16. Mounted in the housing 256 is an inflatable bellows 260 having an upper portion 262 projecting upwardly through the opening 258. Mounted on the top end of the bellows 260 is a smooth, horizontal disk 264 for engaging the bottom surface 250b of the sheet 250. The interior of the bellows 260 is coupled to a regulatable source 266 of pressurized air. The bellows 260 is maintained in a substantially vertical position, as shown in FIG. 11, against any forces applied to the disk 264 by the moving sheet by means of a stabilizer arm 268 having one end 270 attached to the upper portion 262 of the bellows and another end 272 secured to the housing 256. The stabilizer arm 268 may be made of relatively thin rigid material such as sheet metal or plastic hinged at each end or, preferably, may be made of a thin flexible sheet of woven fabric, plastic or the like. In either case, the small up and down movements of the upper portion 262 of the bellows are readily accommodated.

Pressurized air admitted to the interior of the bellows 260 from the source 266 urges the disk 264 into contact with the bottom surface of the sheet 250 thereby compressing the measurement region of the sheet in the vicinity of guide ring 162, that is, the region of sheet containing the area sensed by the optical sensor system 16. The force exerted by the bellows 260 may be controlled by regulating the pressure of the air admitted to the bellows to simulate the forces exerted by various laboratory testers. As a further alternative, it will be evident that air flow may be provided to the upper contact surface of the disk 264 to create an air bearing between the disk and the bottom surface of the sheet to reduce friction and eliminate marking of the sheet.

Process Control

To control the smoothness of paper during its fabrication, the output of the on-line surface sensor 10 of the present invention can be used to control one or more of the many papermaking process parameters that determine the smoothness or texture (as in the case of tissue) of the final product. The specific process parameters selected for control will depend on the paper product being produced.

(1) Coated Fine papers

Various strategies may be used to control the smoothness of coated fine paper, that is, offset and rotogravure printing grades which have light and medium weight coatings. Many of these same strategies apply to the control of the smoothness of the sheet surfaces of other paper products including newsprint, linerboard, machine glazed paper, and so forth as will be explained below.

The control strategies for coated fine papers may include the following:

(a) Filler Content—Filler or ash is added to paper to fill voids and thus smooth the surface. The smoothness measurement made by the on-line surface sensor of the present invention may be used to control the amount of filler to meet a smoothness set point.

(b) Coat Weight—Paper is often coated to provide a smooth printing surface. Coat weight control by differential basis weight or differential ash is well known. However, when the purpose of the coating is to provide a smooth surface, control in response to the measurement of smoothness of the coated surface is a more logical choice.

(c) Calendering—Calendering, which smooths the paper surface by rolling it between either hard or soft rolls, is controlled by:

(i) Pressure—The basic pressure of the calender is determined by the roll weight. The cross direction (CD) distribution of pressure can be controlled by:

[a] Nip Relief—The pressure can be reduced by nip relief at the bearings on either or both ends of the roll. Nip relief provides some means of CD control by adjusting each end independently.

[b] Crown—Increasing the crown of a roll puts more pressure on the middle of the sheet than along the edges. Crown can be increased by increasing the oil pressure inside the roll. Combined with nip relief this provides a three zone CD control, i.e., both ends and the middle.

(ii) Temperature—Smoothness of paper is affected by the temperature of the calender roll. Higher roll temperature produces a smoother surface. Roll temperature can be controlled by:

[a] Induction Heating—The temperature of the surface of the calender roll may be controlled by a magnetic induction heating system such as "CalCoil", a trademark of Measurex Corporation, Cupertino, Calif., U.S.A., for induction heater control actuators for calenders. Such a system is disclosed in U.S. Pat. No. 4,384,514. An array of such heaters across the roll provides CD smoothness control by heating the roll based on CD surface smoothness measurements made by the sensor disclosed herein.

[b] Oil Temperature—The temperature of a calender roll is affected by the temperature of the oil fed to the roll. However, this control strategy may be less effective than induction heating because of the thermal inertia associated with changing the oil temperature.

(d) Formation—Formation refers to the distribution of fibers in the sheet. Poor formation means that there are clumps of fibers in the sheet. When there is poor formation it is difficult to obtain a smooth surface. Formation can be controlled by controlling the consistency, that is, the percent dry fiber content, of the stock slurry in the headbox. Generally, lower consistency results in better formation. For CD formation control, some systems are provided with CD control of the dilution of the stock slurry in the headbox. It is usually desirable to run as high a consistency in the headbox as possible, since the papermaking machine can then be run faster thereby increasing production. One control strategy is to maintain consistency as high as possible while still maintaining a target smoothness. Since smoothness is affected by several things besides formation, a formation sensor should be used in conjunction with the smoothness sensor, so formation can be independently determined, when smoothness targets are not achieved.

Figure 12:
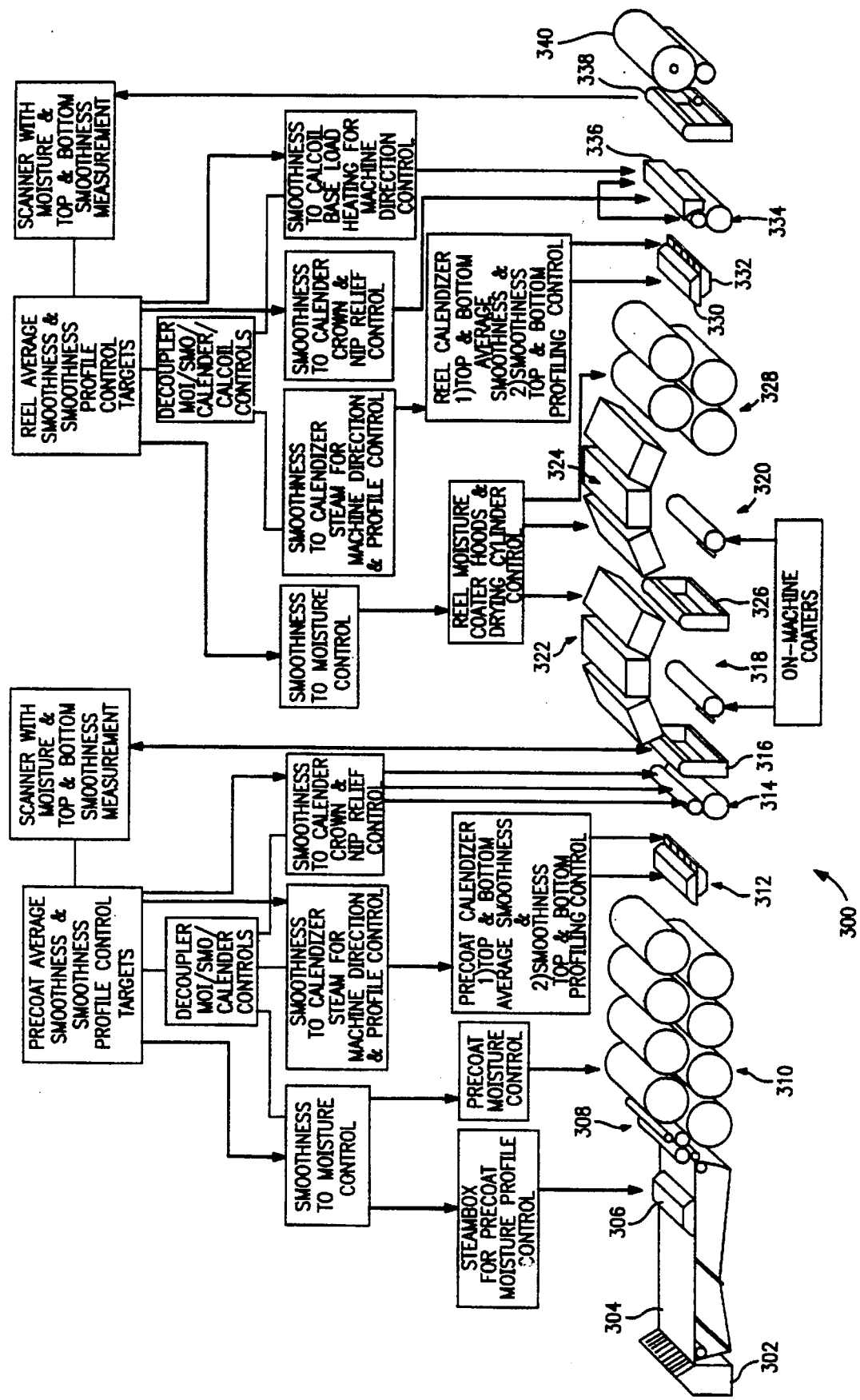
FIG. 12 is a schematic view of a printing grade papermaking machine showing the manner in which the surface sensor of the invention may be used to control various smoothness-determining elements of the papermaking machine.

FIG. 12 shows schematically a machine 300 for making coated fine paper having surfaces whose smoothness is controlled using certain of the strategies outlined above. The papermaking machine 300 includes a headbox 302 to which stock is supplied by means of a pump (not shown). The headbox 302 discharges pulp through a slice lip whose cross direction profile can be controlled in a manner well known in the art. The pulp discharged from the headbox 302 is deposited onto an endless wire screen belt ("wire") 304, the stock so deposited being in the form of a continuous layer or web of paper stock from which a continuous sheet of paper is ultimately formed. The water and other material which drain from the wire 304 is collected in a reservoir (not shown) beneath the wire 304 and returned to the headbox 302. However, the majority of the fiber is left behind on the wire to form a set sheet of paper.

Positioned over the paper sheet on the wire 304 is a steambox 306. Steam discharged from the steambox 306 raises the temperature of the sheet thereby lowering the viscosity of the fibrous mass increasing its drainage rate. The steambox 306 is provided with a plurality of nozzles for cross direction moisture control. After leaving the wire 304, the sheet passes through a press section 308 consisting of a plurality of rolls which remove a substantial portion of the excess moisture in the sheet. The sheet then passes through the cylinders of a drying section 310 and from there between a pair of precoat "calendizers" 312. Saturated steam, discharged from the calendizers 312 at a low flow rate, softens the surface of the sheet for better surface finish. As is the case with most of the processing elements along the sheet path in the papermaking machine 300, the calendizers 312 are provided with cross directional control. The sheet next passes through a calender stack 314 comprising a vertical array of rolls which further smooth the surfaces of the sheet. The sheet then passes through a first, conventional scanner 316 having scanning heads housing a moisture sensor and top and bottom smoothness sensors in accordance with the invention described herein. The papermaking process to this point is termed the "wet end" of the process.

As shown in FIG. 12, various smoothness control strategies based on measurements made by the smoothness sensors carried by the scanner 316 may be employed and these are described in the various boxes in FIG. 12 associated with the wet end of the paper making process. The ways in which control over the various stages 306, 310, 312 and 314 of the wet end process may be exercised in response to the moisture and smoothness measurements made at the scanning station 316 are all well known in the art and need no elaboration.

Continuing with the paper making process of FIG. 11, after leaving the scanner 316 the paper sheet passes through a pair of coating stations 318 and 320 at which coatings are applied to the top and bottom surfaces of the paper sheet. As is well known in the art, these coatings may contain, for example, clay or $CaCO_3$ pigments together with a starch or latex binder. The coating stations 318 and 320 include hoods 322 and 324, respectively, which blow high velocity hot air on the surfaces of the sheet to accelerate drying of the coatings. Between the coating stations 318 and 320 is a second conventional scanner 326 containing coat weight sensors for measuring and controlling the amount of coating materials applied to the sheet.

Following the coating station 320, the paper sheet enters a drying section 328 comprising a series of cylinders for further drying the coatings. The drying section 328 is followed by top and bottom steam calendizers 330 and 332 and a calendar stack 334 which, for the sake of illustration, is shown as comprising two rolls. The CD distribution of pressure exerted by the rolls of calender stack 334 may be controlled by varying the nip relief and/or crown. To control caliper and further improve smoothness of the surfaces of the sheet, the nip between the rolls (and therefore the pressure applied to the sheet) can be varied using an inductive heater 336 of the type disclosed in the aforementioned U.S. Pat. No. 4,384,514. The heater 336 is positioned proximate one of the rolls of the calender stack 334 and is capable of CD temperature control. The sheet then passes through a third, conventional scanner 338 which again measures moisture and top and bottom smoothness, which measurements are used for the control of the various dry end stages as shown and described in FIG. 12. The dry end scanner 338 is followed by a wind-up reel 340 for storing the paper sheet until it is converted for further use. The ways in which control of the dry end stages 322, 324, 328, 330 and 334 may be effected in response to smoothness and moisture measurements made at the scanning station 338 are all well known in the art.

It will be appreciated by the skilled artisan that the "control targets" and scanner measurements described in FIG. 12 (as well as the figures that follow) are presented to a computer system (not shown) having control outputs connected to actuators associated with the controls of the various stages (306, 310, 312 and so forth) of the papermaking machine 300. Further, as shown in FIG. 12 and in subsequent figures, it will be understood by those skilled in the art that "decoupling" of the various controls is provided by the computer system. Such "decoupling" is required to provide compensations for the interaction between the various controls.

(2) Newsprint

In the case of newsprint, using the on-line sensor of the present invention for generating smoothness control signals, the target smoothness may be achieved by controlling utilizing several control strategies, chiefly calender control. The same control strategies used with calender control for printing grades be used for newsprint. However, since calendering is also used for CD caliper control of newsprint, the smoothness control might be limited to MD only. For example, the base calender roll temperature would be determined by the smoothness set point while CD heating would be determined by caliper control.

Figure 13:
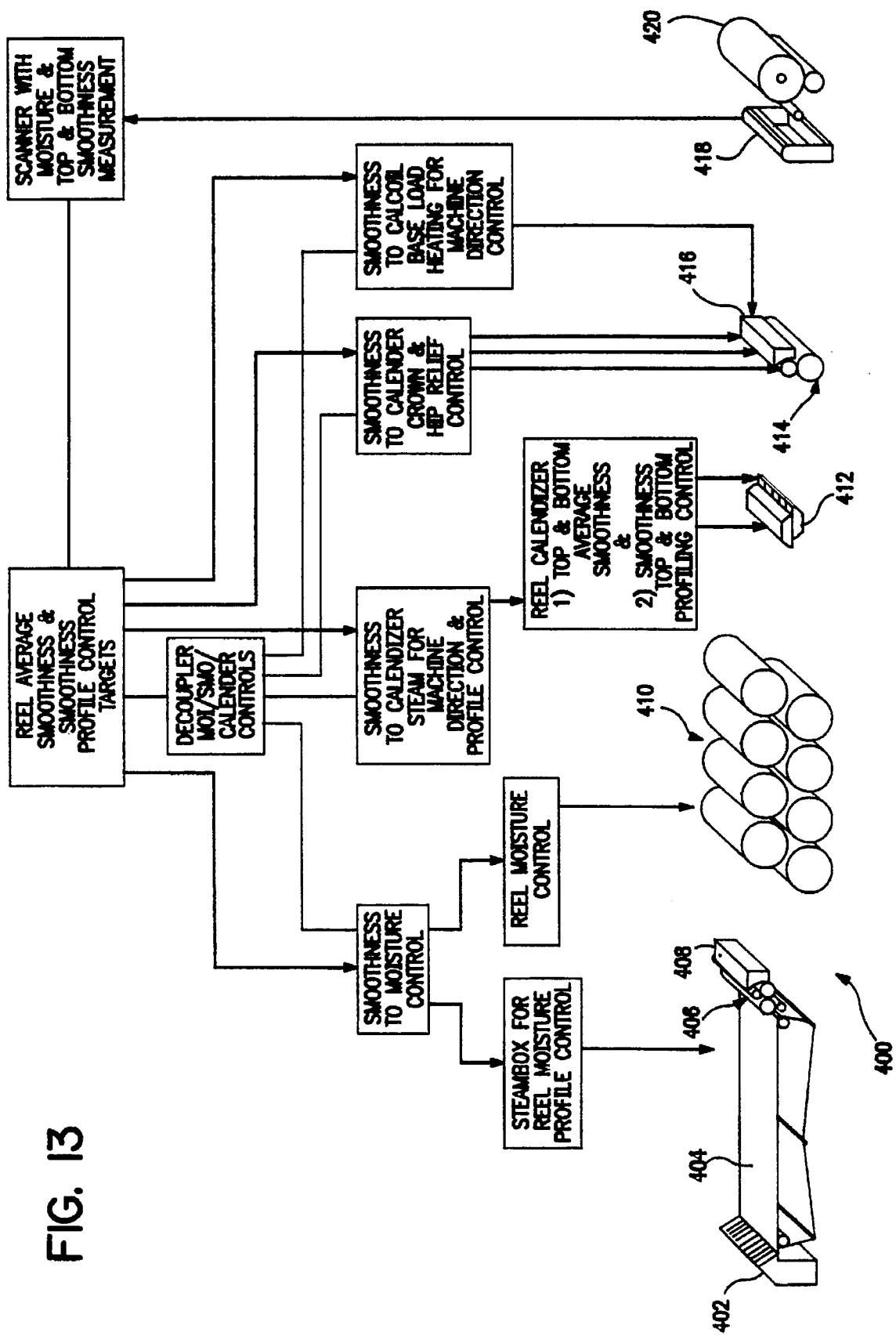
FIG. 13 is a schematic view of a newsprint fabrication machine showing the manner in which the surface sensor of the invention may be used to control various smoothness-determining elements of the machine.

FIG. 13 is a schematic representation of a papermaking machine 400 for producing newsprint. The newsprint papermaking machine 400 is similar in many respects to the machine 300 for producing coated fine papers, the fundamental difference being the omission from the newsprint machine of the sheet coating stations. Thus, the machine 400 includes a headbox 402; a wire 404; a press section 406; a steambox 408 cooperating with the sheet passing through the press section 406; a drying section 410; a calendizer station 412; a calender stack 414 with an associated inductive heater 416; a scanner 418 carrying a smoothness sensor according to the present invention, along with a moisture sensor; and a wind-up reel 420. Besides calender control, control over stages 408, 410 and 412 of the newsprint machine may be achieved using smoothness measurements as shown and described in FIG. 13.

(3) Linerboard

Output signals from the smoothness sensor of the present invention may be used to control various stages of the process for making linerboard. To provide a smooth printing surface on linerboard, a thin top layer having a smooth finish may be also applied on top of the thicker base sheet. Both CD and MD smoothness control of the top layer may be achieved. Calendering is also used to smooth linerboard and control of this stage would be the same as with printing grades.

Figure 14:
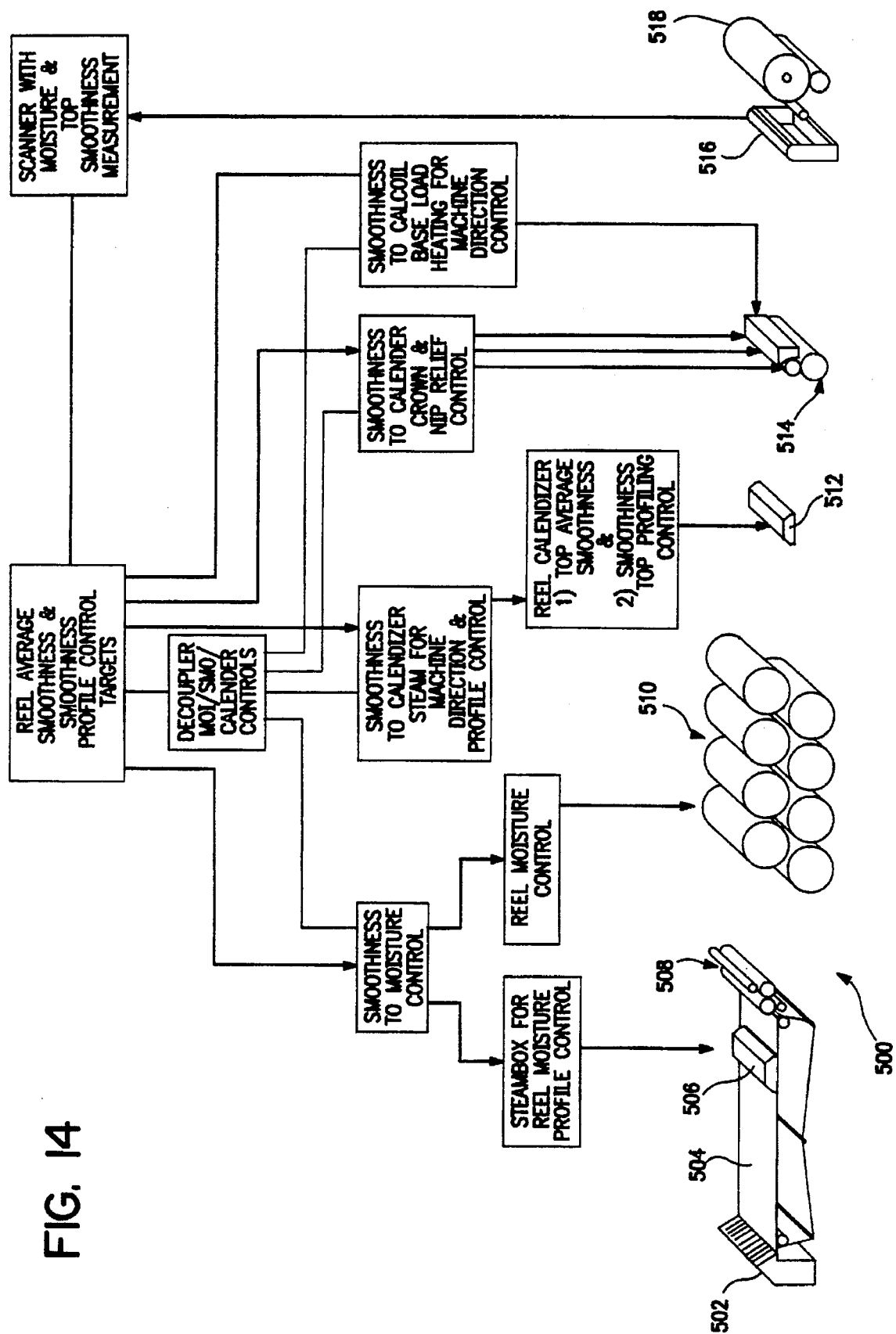
FIG. 14 is a schematic view of a linerboard fabrication machine showing the manner in which the surface sensor of the invention may be used to control various smoothness-determining elements of the machine.

Turning to FIG. 14, there is shown schematically a portion of a papermaking machine 500 for fabricating linerboard. The liner board fabricating machine 500 is similar to the newsprint machine 400 and includes a headbox 502; a wire 504; a steambox 506; a press section 508; a drying section 510; a calendizer station 512; a calender stack 14; a scanner carrying a smoothness sensor as described herein along with a moisture sensor; and a wind up reel 518. The various control strategies are summarized in FIG. 14.

(4) Machine Glazed

The smoothness of multilayer and Kraft paper is often controlled by means of a machine glazed cylinder. A machine glazed cylinder is a highly polished cylinder to which the paper sheet is pressed to impart a smooth, glossy surface. The degree of smoothing can be controlled by the moisture content of the paper going into the roll. Moisture can be controlled in both MD and CD by a CD sectioned steambox which controls sheet moisture content by drying the sheet with hot steam applied to the sheet. By applying different amounts of steam in each section, CD control is achieved. Moisture can also be controlled by means of a water shower which adds moisture to the sheet by spraying water from a CD array of nozzles. Still further, differential steam pressure control of the dryers, prior to the machine glazed cylinder, can be used to control moisture of the sheet going into the machine glazed cylinder.

Figure 15:
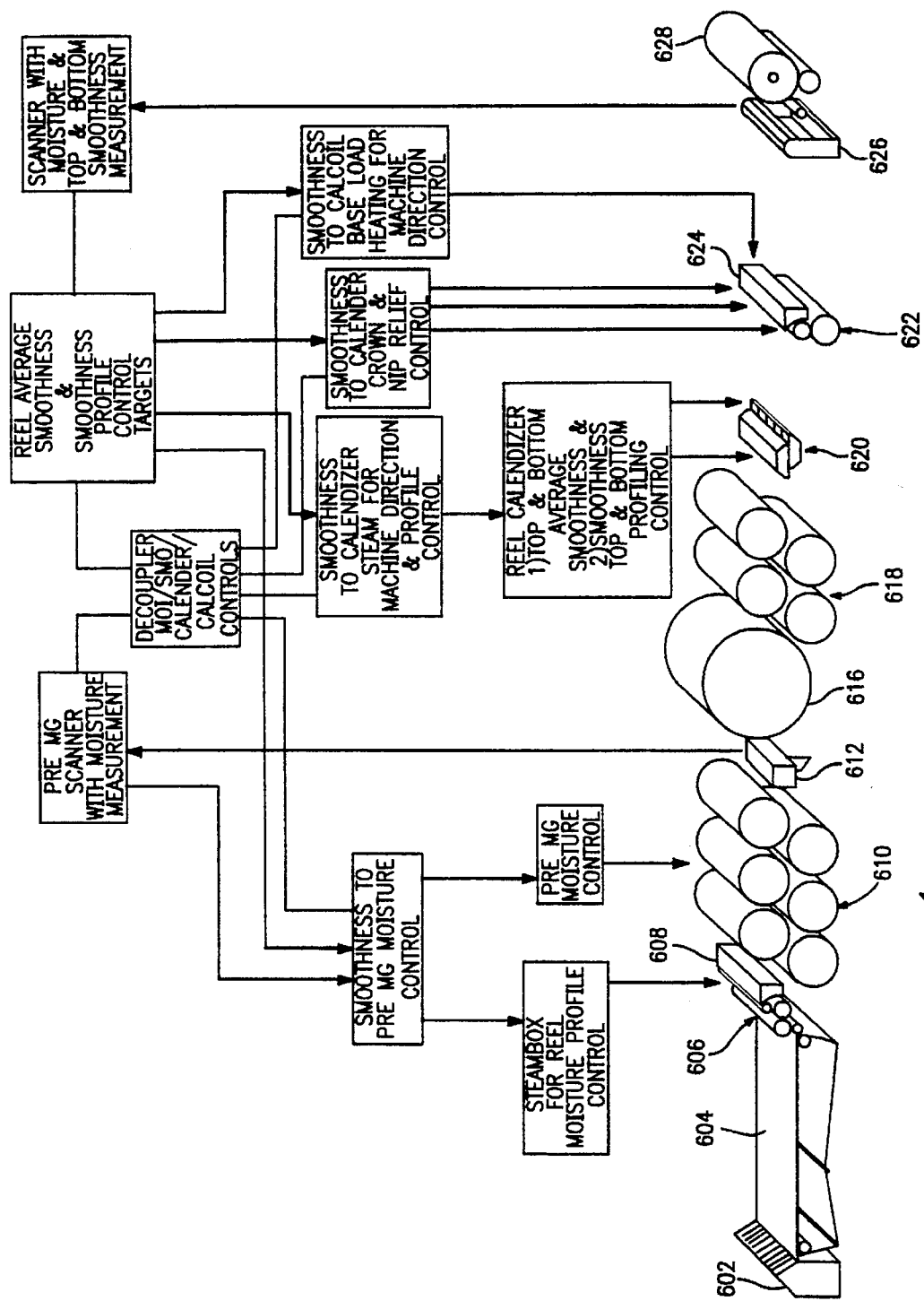
FIG. 15 is a schematic view of a machine glazed paper fabrication machine showing the manner in which the surface sensor of the invention may be used to control various smoothness-determining elements of the machine.

FIG. 15 shows schematically a machine glazed papermaking machine 600 and the manner in which the smoothness of the surfaces of multilayer and Kraft paper products may be controlled utilizing the smoothness sensor of the invention.

The machine 600 includes, generally, a headbox 602; a wire 604; a press section 606; a steambox 608; a drying section 610; a first, conventional scanner 612; a machine glazed cylinder 616; a second drying section 618; a calendizer section 620; a calender stack 622 with an associated induction heater 624; a second conventional scanner 626; and a wind up reel 628. The first scanner carries a sheet moisture sensor while the second scanner carries both a moisture sensor and a smoothness sensor according to the invention described herein. The various control strategies are summarized in FIG. 15.

(5) Supercalendered Fine paper

Figure 16:
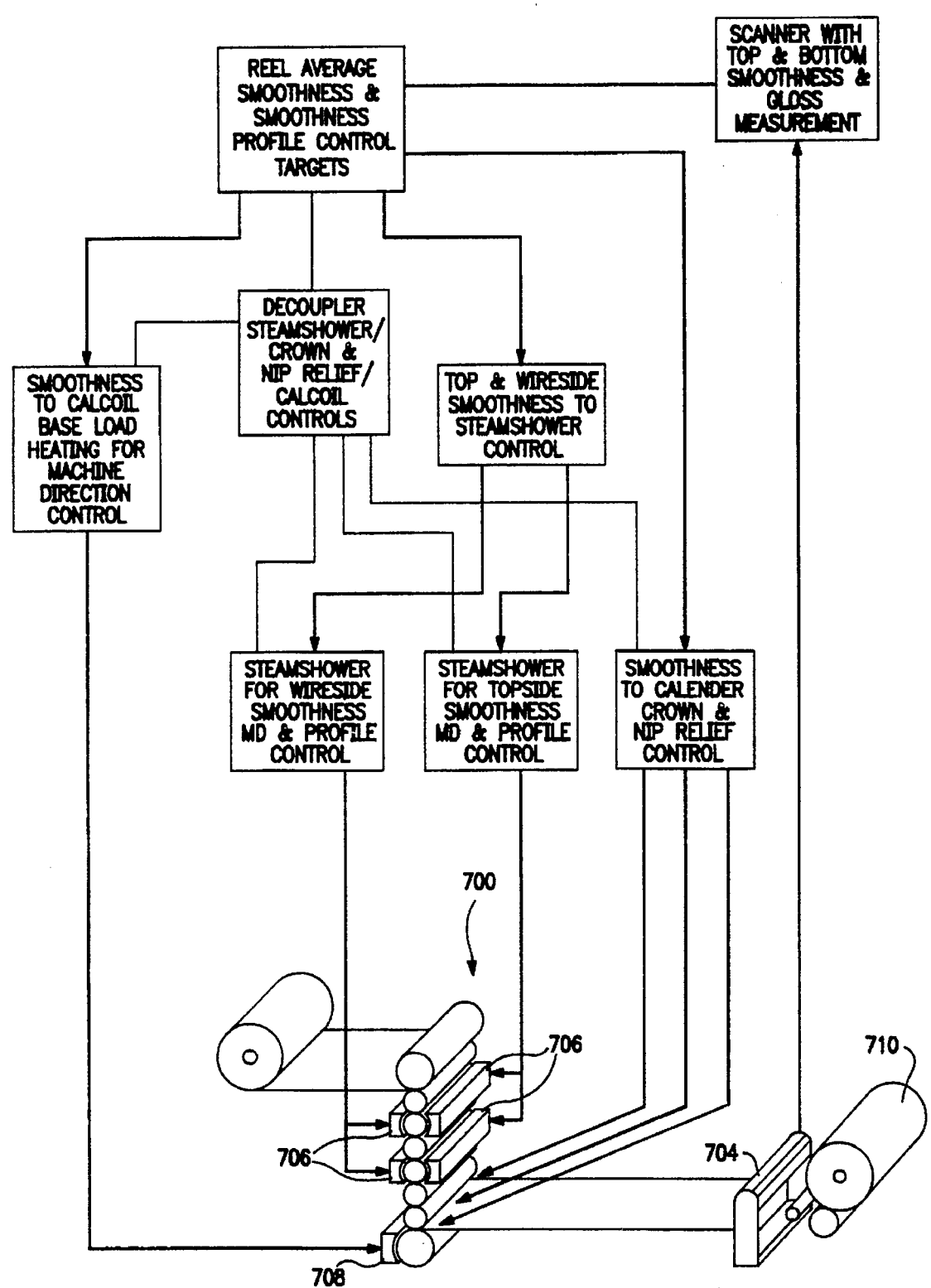
FIG. 16 is a schematic view of a fine paper supercalender machine showing the manner in which the surface sensor of the invention may be used to control various smoothness-determining elements of the machine.

With reference to FIG. 16, the control of the smoothness of fine papers through a supercalender (calenders for making extremely smooth paper) may be effected by using the smoothness sensor of the invention to control the supercalender (either off-machine, as shown in FIG. 16, or on-machine). The paper enters a supercalender stack 700 which comprises a vertical array of rolls which alternate between chilled rolls and filled rolls. Various smoothness control strategies supervised by a computer based on measurements made by the smoothness sensor carried by a conventional scanner 704 may be employed and these are described in the various boxes associated with FIG. 16. For example, saturated steam at a low flow rate from multiple steam showers 706 controlled by the computer 702 and mounted on both sides of the sheet, soften the surfaces of the sheet for a better surface finish. The CD distribution of pressure exerted by the rolls of the supercalender stack 700 may be controlled by varying the nip relief and/or crown to further improve smoothness. To control caliper and further improve the smoothness of the surfaces of the sheet, the nip between the rolls (and therefore the pressure applied to the sheet) can be varied using an inductive heater 708 of the type disclosed in the aforementioned U.S. Pat. No. 4,384,514. The heater 708 is positioned is positioned proximate one of the rolls of the supercalender stack and is capable of CD temperature control. After the sheet passes through the scanner 704, it is stored on a wind-up roll 710.

Control strategies similar to those summarized in FIG. 16 can be used to control the smoothness of glassine and supercalendered magazine paper.

(6) Tissue

In the manufacture of tissue, creping is an important means of increasing the tissue's texture and softness. Creping is the process of putting small folds in the sheet. The depth and spacing of the folds gives the texture to the sheet. A sheet with large spacing between folds will feel coarser than a sheet with close spacing.

Creping occurs during the drying process when the tissue is scraped off the dryer drum (called the Yankee cylinder) with a doctor or creping blade. Creping is determined by the angle of the doctor blade and the degree of adhesion to the Yankee cylinder. Adhesion is provided by a polymer continuously sprayed onto the outer surface of the Yankee cylinder. The angle of the doctor blade is ground into the blade and cannot be changed once it is installed on the machine. As the blade wears, the angle changes, which affects the creping.

Several techniques can be used to control the creping process, among which are:

(a) Control of the flow of the polymer adhesive spray. By using variable flow spray nozzles across the Yankee cylinder, the amount of adhesive polymer can be controlled in both MD and CD.

(b) Control of the angle of the creping or doctor blade.

(c) Control of the moisture content of the sheet going onto the Yankee cylinder. A moister sheet going onto the Yankee cylinder will have less adhesion than a drier sheet.

Figure 17:
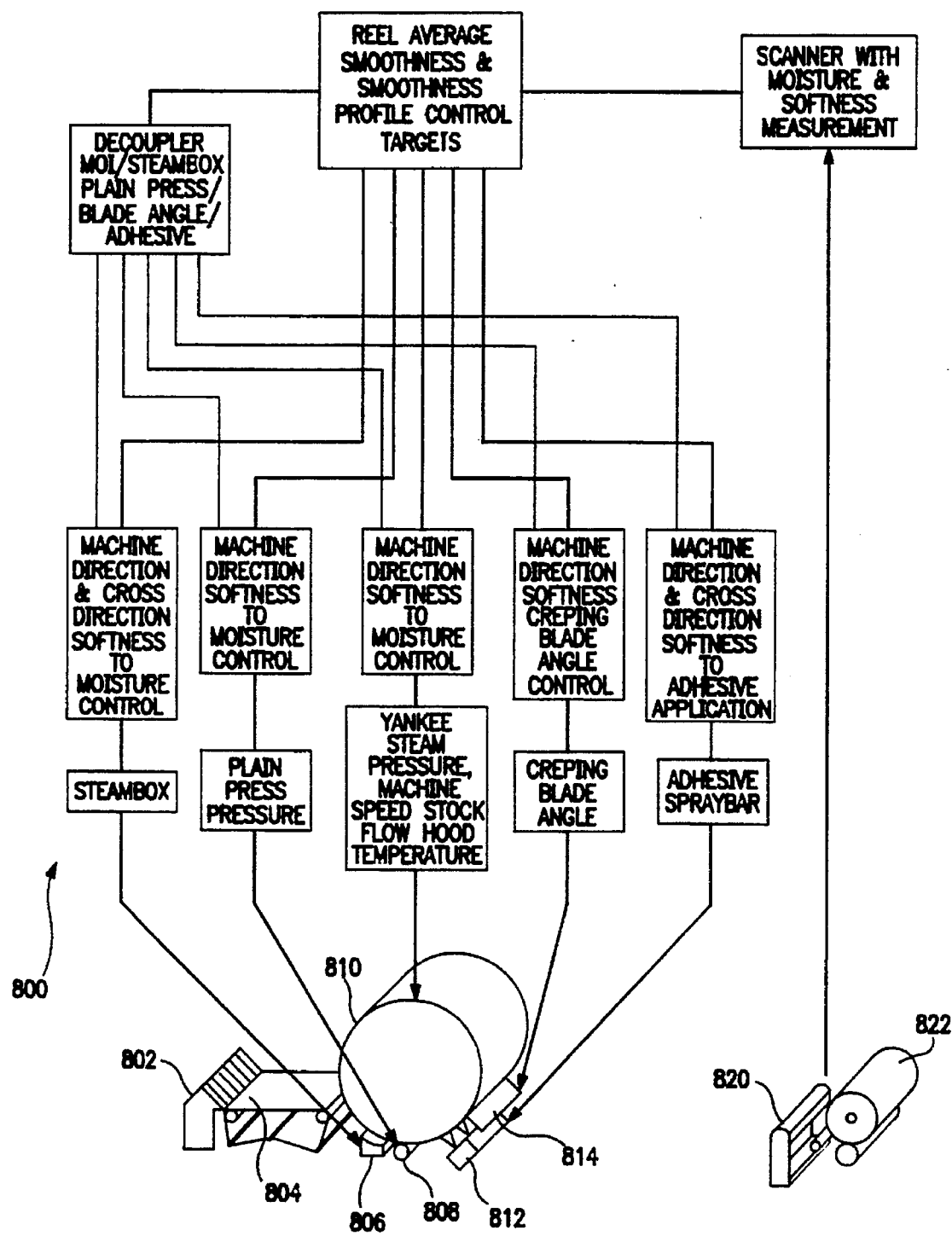
FIG. 17 is a schematic view of a tissue fabrication machine showing the manner in which the surface sensor of the invention may be used to control various elements of the machine which determine the degree of crepe and softness of the tissue.
Figure 18:
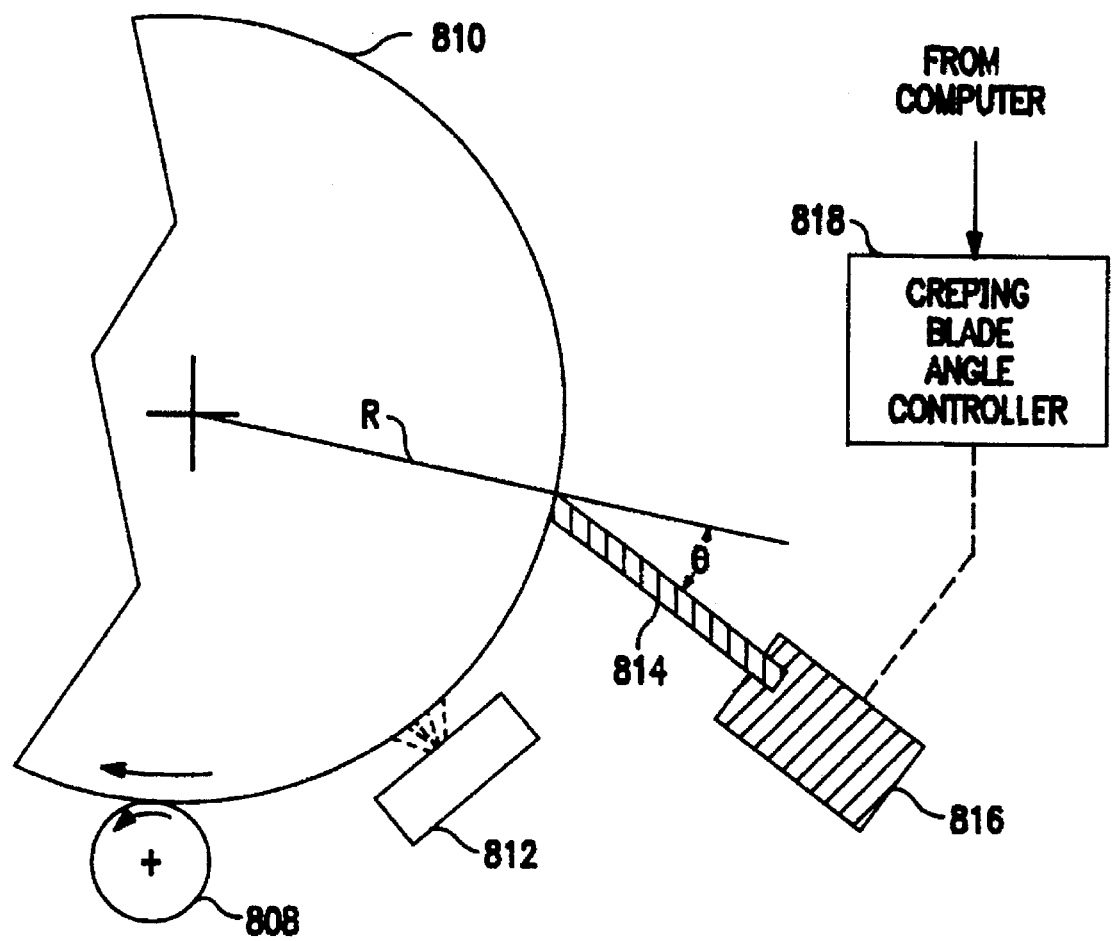
FIG. 18 is a side elevation view of a portion of the tissue machine of FIG. 17.

FIG. 17 shows schematically a machine 800 for fabricating tissue and the various ways in which the process can be controlled to control the creping properties of the tissue. The machine 800 includes a headbox 802 and a wire 804. The tissue sheet exiting the wire 804 travels around a steambox 806 which discharges saturated steam against the tissue sheet to control drying thereof. From the steambox 806 the papersheet travels around a plain press pressure roll 808 which in the example of the machine under consideration rotates in a counterclockwise direction. The sheet passes through a nip defined by the plain press roll 808 and the Yankee cylinder 810, a large heated cylinder which in FIG. 17 rotates clockwise. As is well known in the art, the surface of the Yankee cylinder is coated with a polymer adhesive applied to the outer surface of the Yankee cylinder by means of an adhesive spray bar 812. By virtue of the polymer adhesive, the tissue sheet adheres to the surface of the cylinder. The elevated temperature of the cylinder drives off moisture from the tissue sheet. The pressure of the plain press roll 808 may be controlled to control the softness of the tissue. A reduction in the pressure exerted by the plain press roll results in increased softness. The tissue sheet adhered to the outer surface of the Yankee cylinder eventually encounters a creping or doctor blade 814 which, also as well known in the art, strips the tissue sheet from the surface of the Yankee cylinder. It is this stripping process which is the primary agency by which folds or creping are imparted to the tissue sheet making it soft. As shown in FIG. 18, the creping or doctor blade 814, carried by an adjustable support 816, is disposed at an angle $\theta$ to a radius, R, of the Yankee cylinder 810. Variations in the angle $\theta$ are controlled by a creping blade angle controller 818 connected to the output of the supervisory computer. The angle of the blade 814 determines the degree of creping and hence the softness of the tissue. From the doctor blade 814, the sheet travels through a conventional scanner 820 which carries a moisture sensor along with a surface characteristic sensor in accordance with the present invention for measuring the heights of the folds in the tissue sheet being fabricated for various ranges of fold scale sizes. From the scanner 820 the tissue travels to a wind-up roll 822. The output of the surface sensor of the scanner 820 may be used to control one or more of the various stages of tissue fabrication, including, as shown and described in FIG. 17, the steambox 806; the plain press roll 808; various Yankee cylinder parameters including steam pressure, machine speed, stock flow and hood temperature; the polymer adhesive spray bar 812 and the angle of the creping blade 814. Again, the specific ways in which these tissue machine elements can be controlled are known.

The surface sensor of the invention can also be used to monitor the condition of the doctor blade 814. As the blade wears, the creping folds become deeper and further apart. These parameters can be continuously measured by the surface sensor 10 and an indication provided to the mill operator of the estimated blade life remaining. Further, when the creping fold parameters reach predetermined limits, an alarm can be triggered alerting the operator that the blade needs replacement.

What is claimed is:

1. An apparatus for the continuous, on-line measurement of a property of a surface of a moving sheet, said property being characterized by surface features having various scale sizes and heights, the apparatus comprising:

a laser light source;

means for focusing incident light from the laser source along an optical path intercepting the surface of the moving sheet to illuminate a light spot on said surface;

means for collecting light scattered at a non-specular angle from the illuminated spot;

a photosensitive detector responsive to a spectrum of frequencies produced by the various surface feature scale sizes, the detector having an output;

means for focusing the collected scattered light on said photosensitive detector, the output of the detector providing an output signal representing variations of the height position of the light spot on the surface of the moving sheet; and a plurality of channels each including a filter responsive to the output signal of the detector, said filters having different cut-off frequencies for passing different frequency spectra representing different ranges of surface features scale sizes.

2. An apparatus, as defined in claim 1, including:

means for monitoring the speed of the moving sheet and providing an output indicative of said speed;

and in which:

the cut-off frequency of each of the filters is varied in response to variations in the output of the sheet speed monitoring means.

3. An apparatus, as defined in claim 1, in which:

the photosensitive detector comprises a balance detector generating a pair of signals, the detector output signal being proportional to the difference between the signals of said pair of signals.

4. An apparatus, as defined in claim 3, including:

means between the detector and the at least one channel for processing the pair of detector signals, said signal processing means providing an output that is a function of the ratio of the difference between the pair of signals to the sum of the pair of signals.

5. An apparatus, as defined in claim 3, in which:

the balance detector comprises a pair of side-by-side photosensitive cells separated by a small linear gap, and in which the light focused on the balance detector bridges the gap so as to illuminate to a greater or a lesser extent the detector cells substantially in accordance with the height position of the light spot illuminating the surface of the moving sheet.

6. An apparatus, as defined in claim 5, in which:

the linear gap separating the balance detector cells is disposed at an angle to the direction of movement of the light spot incident on the detector to extend the range of the detector.

7. An apparatus, as defined in claim 1, in which:

each filter comprises a high pass filter.

8. An apparatus, as defined in claim 7, including:

means for monitoring the speed of the moving sheet and for providing an output indicative of said speed;

and in which:

said high pass filter comprises an RC filter having an input connected to the output of the photosensitive detector, a variable resistor, and an output across the variable resistor, and including means for controlling the value of the resistor in response to the output of the speed monitoring means.

9. An apparatus, as defined in claim 8, in which:

said resistor value controlling means comprises an XY multiplier circuit having a first input connected to the output of the sheet speed monitoring means and a second input connected to the output of the filter.

10. An apparatus, as defined in claim 1, in which:

each filter comprises a bandpass filter.

11. An apparatus, as defined in claim 1, which includes:

means defining a reference surface along which the surface of the sheet is adapted to move in close proximity, said reference surface lying substantially in a plane at which the incident light focusing means focuses the light spot illuminating the surface of the sheet; and a sheet stabilizer for maintaining the surface of the moving sheet in close proximity to the reference surface.

12. An apparatus, as defined in claim 1, which includes:

means defining a reference surface along which the surface of the sheet is adapted to move in close proximity, said reference surface lying in a plane at which the incident light focusing means focuses the light spot illuminating the surface of the sheet;

a standardizing member having an optical standardizing surface; and means for moving said standardizing member into an off-sheet standardizing position in which the optical standardizing surface is positioned substantially in the plane of the reference surface.

13. An apparatus, as defined in claim 12, further including:

means for oscillating the position of the standardizing member in a direction along the optical axis of the incident light at at least one predetermined frequency and at least one predetermined amplitude representing, respectively, at least one surface feature scale size and at least one surface feature height variation.

14. An apparatus, as defined in claim 1, in which:

the filter of each channel has an output; and each channel includes an RMS AC to DC converter connected to the output of the filter associated with that channel, each said RMS AC to DC converter providing a channel output.

15. An apparatus, as defined in claim 14, in which:

each filter is a high pass filter having a predetermined cutoff frequency;

the apparatus further including:

an arithmetic unit connectable to the outputs of two of the channels, the arithmetic unit providing an output indicative of the height position variations within the scale size range corresponding to the cutoff frequencies of the filters in said two channels.

16. An apparatus, as defined in claim 1, in which:

the light spot produced on the surface of the sheet by the incident light focusing means has a width no greater than about 20 micrometers.

17. An apparatus, as defined in claim 1, in which:

the plurality of channels span a corresponding plurality of contiguous scale size ranges.

18. An apparatus, as defined in claim 1, in which:

each filter comprises a low pass filter.

19. An apparatus, as defined in claim 1, in which:

the lowest cut-off frequency is above the frequency of low frequency phenomena such as sheet flutter.

20. An apparatus, as defined in claim 1, in which:

the surface property comprises creping.

21. An apparatus for the continuous, on-line measurement of the topographical features of a surface of a moving sheet, said features having various scale sizes and heights, the apparatus comprising:

a laser triangulation position sensor for illuminating a light spot on the surface of the moving sheet and including a detector responsive to an image of the light spot reflected from the surface substantially along an optical axis of reflection, the detector comprising a pair of cells separated by a linear gap, the cells defining an active photosensitive area intercepting the reflection axis so that the image received by the detector bridges the gap to illuminate to a greater or a lesser extent the detector cells thereby sensing position deviations of the image substantially in accordance with variations in the height position of the light spot illuminating the surface of the moving sheet, the image being displaceable along an axis on the active area intercepting the linear gap, the detector having an output for providing a signal representing variations of the height position of the light spot illuminating the surface of the moving sheet, the linear gap being disposed at an angle lying between the image displacement axis and an axis orthogonal thereto, the angular orientation of the linear gap extending the measurement range of the detector.

22. An apparatus, as defined in claim 21, in which the sensor includes:

a source of laser light;

means for focusing light from the laser source along an optical path of incident light substantially perpendicular to the surface of the moving sheet to illuminate the light spot on said surface; and means for collecting scattered light reflected at a non-specular angle from the illuminated light spot and focusing the collected light on the active area of the detector substantially along the reflection axis.

23. An apparatus, as defined in claim 21, in which:

the detector is responsive to a spectrum of frequencies produced by surface feature scale sizes of at least 20 micrometers.

24. An apparatus, as defined in claim 21, in which:

each cell of the detector is adapted to generate an electrical signal indicative of the extent of illumination of that cell by the reflected image, the detector output signal being substantially proportional to the difference between the signals generated by the cells of the detector.

25. An apparatus, as defined in claim 21, in which:

each cell of the detector is adapted to generate an electrical signal indicative of the extent of illumination of that cell by the reflected image, the detector output signal being a function of the ratio of the difference between the signals generated by the cells to the sum of said signals.

26. An apparatus, as defined in claim 21, in which:

the light spot illuminated on the surface of the moving sheet has a width no greater than about 20 micrometers.

27. An apparatus, as defined in claim 21, which includes:

at least one channel having a filter responsive to the output signal of the detector for filtering out variations in the detector output signal resulting from low frequency phenomena such as sheet flutter and passing frequencies in the detector output signal representing a range of surface feature scale sizes.

28. An apparatus, as defined in claim 27, including:

a plurality of channels each including a filter, said filters having different cut-off frequencies for passing different frequency spectra representing different ranges of surface feature scale sizes.

29. An apparatus, as defined in claim 28, including:

means for monitoring the speed of the moving sheet and providing an output indicative of said speed;

and in which:

the cut-off frequency of each of the filters is varied in response to variations in the output of the sheet speed monitoring means.

30. An apparatus, as defined in claim 29, in which:

each filter comprises a high pass filter.

31. An apparatus, as defined in claim 29, in which:

each filter comprises a bandpass filter.

32. An apparatus, as defined in claim 28, in which:

the filter of each channel has an output; and each channel includes an AC to DC converter connected to the output of the filter associated with that channel, the AC to DC converter of each channel generating a DC output signal indicative of the true RMS value of the filtered signal.

33. A method for measuring the surface features of a moving sheet, said surface features having various scale sizes and heights, said method comprising the steps of:

focusing light from a source along an optical path intercepting the surface of the moving sheet to illuminate a light spot on said surface;

collecting light scattered at a non-specular angle from the illuminated spot;

providing, in response to the collected light, a signal representing variations in the heights of said surface features and having a frequency spectrum produced by the various scale sizes of said surface features; and processing the signal to produce a plurality of channels covering a total frequency range selected according to the total range of surface feature scale sizes of interest, each channel covering a surface feature scale size range that is different than the surface feature scale size ranges of the remaining channels.

34. A method, as defined in claim 33, further including the steps of:

providing a filtering cutoff frequency for each channel;

monitoring the speed of the moving sheet; and controlling the cutoff frequency of each channel in response to variations in the speed of said sheet.

35. A method, as defined in claim 33, further including the steps of:

filtering the signal to produce a plurality of filtered outputs, each of said filtered outputs being associated with one of the plurality of channels, wherein each filtered output is derived from said signal by filtering out all frequency components of the first signal above a predetermined frequency, and wherein the predetermined frequency is different for each filtered output.

36. A method, as defined in claim 35, further including the step of:

producing a separate DC output from each filtered output, each DC output being indicative of the true root mean square value of a filtered output.

37. A method, as defined in claim 33, further including the steps of:

storing values of said signal during predetermined, successive data acquisition time intervals, each said time interval having a beginning;

providing successive values of the data acquired during successive time intervals;

measuring the speed of the sheet;

adjusting the beginning of said successive time intervals in response to the measured speed of the sheet;

obtaining the difference between the values of the data acquired during successive time intervals; and averaging the differences of the values acquired during successive time intervals.

38. A method, as defined in claim 33, in which:

the plurality of channels span a corresponding plurality of contiguous scale size ranges.

39. A method, as defined in claim 33, further including the steps of:

monitoring the speed of the moving sheet; and adjusting each channel in response to speed of the sheet to hold substantially constant the scale size range of each channel.

40. A method, as defined in claim 33, in which:

the moving sheet comprises paper and the surface features comprise creping.

41. An apparatus for the continuous on-line measurement of a characteristic of a surface of a moving paper sheet having opposed surfaces, the apparatus comprising:

a laser triangulation position sensor disposed adjacent one of the sheet surfaces for illuminating a light spot on said sheet surface, the sensor including a detector having an output for providing a signal representing variations of the height position of the light spot illuminating the surface of the moving sheet, the sensor further including a bottom, planar surface; and a backing platform positioned adjacent the other of said sheet surfaces, the backing platform including means for biasing the region of the sheet illuminated by the light spot toward the bottom surface of the sensor to compress said region of said moving paper sheet.

42. An apparatus, as defined in claim 41, in which:

the biasing means comprises an inflatable bellows having opposed end portions, one of the end portions being attached to the platform, the other of the end portions being positioned to urge the sheet toward the bottom surface of the sensor.

43. An apparatus, as defined in claim 42, including:

a stabilizer arm connecting the other end of the bellows to the platform, the stabilizer arm resisting the tendency of the one end of the bellows to be carried along by said moving sheet.

44. An apparatus for the continuous, on-line measurement of a property of a surface of a moving sheet, said property being characterized by surface features having various scale sizes and heights, the apparatus comprising:

a laser light source;

means for focusing incident light from the laser source along an optical path intercepting the surface of the moving sheet to illuminate a light spot on said surface;

means for collecting light scattered at a non-specular angle from the illuminated spot;

a photosensitive detector responsive to a spectrum of frequencies produced by the various surface feature scale sizes, the detector having an output;

means for focusing the collected scattered light on said photosensitive detector, the output of the detector providing an output signal representing variations of the height position of the light spot on the surface of the moving sheet;

at least one channel including a filter responsive to the output signal of the detector for filtering out low frequency variations in the detector output signal and passing frequencies in the detector output signal representing a range of surface feature scale sizes;

means defining a reference surface along which the surface of the sheet is adapted to move in close proximity, said reference surface lying in a plane at which the incident light focusing means focuses the light spot illuminating the surface of the sheet;

a standardizing member having an optical standardizing surface; and means for moving said standardizing member into an off-sheet standardizing position in which the optical standardizing surface is positioned substantially in the plane of the reference surface.

45. An apparatus, as defined in claim 44, further including:

means for oscillating the position of the standardizing member in a direction along the optical axis of the incident light at least one predetermined frequency and at least one predetermined amplitude representing, respectively, at least one surface feature scale size and at least one surface feature height variation.

* * * * *